United States Patent [19]
Beck et al.

[11] Patent Number: 6,056,978
[45] Date of Patent: May 2, 2000

[54] USE OF HYPERIMMUNE MILK TO PREVENT SUPPRESSION OF T-LYMPHOCYTE PRODUCTION

[75] Inventors: Lee R. Beck, Lebanon, Ohio; Atsunori Ishida, Honjo, Japan; Yasunobu Yoshikai, Higashiku, Japan; Shinji Murosaki, Nara, Japan; Chiharu Kubo, Hakata-ku, Japan; Yoshio Hidaka, Tokyo, Japan; Kikuo Nomoto, Higashi-ku, Japan

[73] Assignee: Stolle Milk Biologics, Inc., Cincinnati, Ohio

[21] Appl. No.: 08/419,952

[22] Filed: Apr. 10, 1995

Related U.S. Application Data

[63] Continuation of application No. 08/053,253, Apr. 28, 1993, abandoned, which is a continuation of application No. 07/899,719, Jun. 16, 1992, abandoned.

[51] Int. Cl.$^7$ .................................................. D61K 45/00
[52] U.S. Cl. ................... 424/535; 424/150.1; 424/278.1; 514/878
[58] Field of Search ............................. 424/150.1, 278.1, 424/535; 514/878

[56] References Cited

U.S. PATENT DOCUMENTS

| | | |
|---|---|---|
| 4,879,110 | 11/1989 | Beck et al. . |
| 5,106,618 | 4/1992 | Beck et al. . |

FOREIGN PATENT DOCUMENTS

| | | |
|---|---|---|
| 0380032 | 8/1990 | European Pat. Off. . |
| 9325232 | 12/1993 | WIPO . |

OTHER PUBLICATIONS

Ishida et al., "Consumption of Milk from Cows Immunized with Intestinal Bacteria Influences Age Related Changes in Immune Conpetence in Mice," Journal of Nutrition, 122:1875–1883, published Sep. 1992.
Murasaki et al., "Influence of Intake of Skim Milk from Cows Immunized with Intestinal Bacterial Antigens on Onset of Renal Disease in (NZBX NZW)F, Mice Fed Ad Libitum or Restricted in Energy Intake," Journal of Nutrition, 121:1860–1868, published Nov. 1991.
Murosaki et al 1991 121:1860.
Golay et al 1990 J Clin Nutr. 1014.
Adler, W. et al., Effect of age upon primary alloantigen recognition by mouse spleen cells, *J. Immunol.* 107(5):1357–1362 (1971).
Berg, R., Translocation of indigenous bacteria from the intestinal tract, *Human Intestinal microflora in Health and Disease*, Chapter 15:333–352 (1983).
Bocci, V., Production and role of interferon in physiological conditions, *Biol. Rev.* 56:49–85 (1981).
Chandra, R., Nutritional regulation of immunity and risk of infection in old age, *Immunol.* 67:141–147 (1989).
Gabrielsen, A. et al., Suppression of murine lupus eryhtematosus by Dactinomycin, *Nature* 264:439–440 (Dec. 1976).
Golay, A. et al., Cholesterol–lowering effect of skim milk from immunized cows in hypercholesterolemic patients, *Am. J. Clin. Nutr.* 52:1014–1019 (1990).
Hilpert H. et al., Use of bovine milk concentrate containing antibody to rotavirus to treat rotavirus gastroenteritis in infants, *J. Infect. Dis.* 156(1):158–166 (Jul. 1987).
Hirokawa K. et al., Influence of age of thymic grafts on the differentiation of T cells in nude mice, *Clin. Immunol. & Immunopathol.* 24:251–262 (1982).
Janeway, C., Frontiers of the immune system, *Nature* 333:804–806 (Jun. 1988).
Kato K. et al., Qualitative and quantitative analysis of autoantibody production in aging mice, *Aging Immunol. Inf. Dis.* 1(3):177–190 (1988).
Kubo C. et al., Calorie source, calorie restriction, immunity and aging of (NZB/NZW)F1, mice, *J. Nutr.* 114:1884–1899 (1984).
Makinodan T. et al., Age influence on the immune system, *Adv. Immunol.* 29:287–330 (1980).
Mastromarino, A., Antibiotic radioprotection of mice exposed to supralethal whole–body irradiation, *Radiation Research* 68:329–338 (1976).
Miake S. et al., Protective effect of *Lactobacillus casei* on *Pseudomonas aeruginosa* infection in mice, *Infect. Immun.* 48(2):480–485 (May 1985).
Nomoto K. et al., Augmentation of host resistance to *Listeria monocytogenesis* infection by *Lactobacillus casei*, *J. Clin. Lab. Immunol.* 17:91–97 (1985).
Price G. et al., Immunologic deficiencies in senescence II. Characterization of extrinsic deficiencies, *J. Immunol.* 108(2):413–417 (Feb. 1972).
Tacket C. et al., Protection by milk immumoglobulin concentrate against oral challenge with enterotoxigenic *Escherichia coli*, *N. Engl. J. Med.* 318(19):1240–1243 (May 1988).
Wade A. et al., Aging, idiotype repertoire shifts, and compartmentalization of the mucosal–associated lymphoid system, *Adv. Immunol.* 36:143–188 (1984).
Waldmann, T., Monoclonal Antibodies in Diagnosis and Therapy, *Science* 252:1657–1662 (Jun. 1991).

(List continued on next page.)

*Primary Examiner*—Christina Y. Chan
*Assistant Examiner*—Martha Lubet
*Attorney, Agent, or Firm*—Sterne, Kessler, Goldstein & Fox P.L.L.C.

[57] ABSTRACT

The invention relates to the use of hyperimmune milk derived from milk producing animals hyperimmunized with bacterial antigens including intestinal bacteria. The present hyperimmune milk effectively prevents the decline of immunological functions observed in aging or immunocompromised animals and prevents the translocation of indigenous enteric bacteria from the GI tract of immunocompromised or aged animals, thereby preventing indigenous infection. More specifically, the present hyperimmune milk is administered to an animal in an amount sufficient to effectively prevent translocation of indigenous enteric bacteria in, delay the onset of, lower the rate of, or restore the declining immune functions of, aging or otherwise immunocompromised animals.

10 Claims, 9 Drawing Sheets

OTHER PUBLICATIONS

Welsh, J., et al., Anti–infective properties of breast milk, *J. Pediatr.*, 94(1):1–9 (Jan. 1979).

Yoshikai Y. et al., Increased susceptibility to *Escherichia coli* infection in mice pretreated with *Corynebacterium parvum, Microbiol. Immunol.* 27(3):273–282 (1983).

Ishida et al., "The Defence Effect of the Immunized Milk on the Lowered Immune Function Brought About by Ageing," Abstract No. 20p9, Annual Meeting of Japan Society for Bioscience, Biotechnology and Agrochemistry at Ritsumeikan University, Kyoto, Mar. 1991.

Dialog 351, WPI Accession No. 92–288888/199235, English language abstract of JP 4198136 A. 1992.

English language translation of Japanese Patent No. Hei 2(1990)–331861 1992.

Ishida, A. et al., "Administration of milk from cows immunized with intestinal bacteria protects mice from radiation–induced lethality," *Biotherapy* 5:215–225 (1992).

Yoshikai, Y. et al., "Sequential appearance of T–cell receptor γδ– and αβ–bearing intestinal intra–epithelial lymphocytes in mice after irradiation," *Immunol.* 74:583–588 (1991).

Murosaki, S. et al., "Failure of T cell receptor $V_\beta$ negative selection in murine intestinal intra–epithelial lymphocytes," *Intl. Immunol.* 3(*10*):1005–1013 (1991).

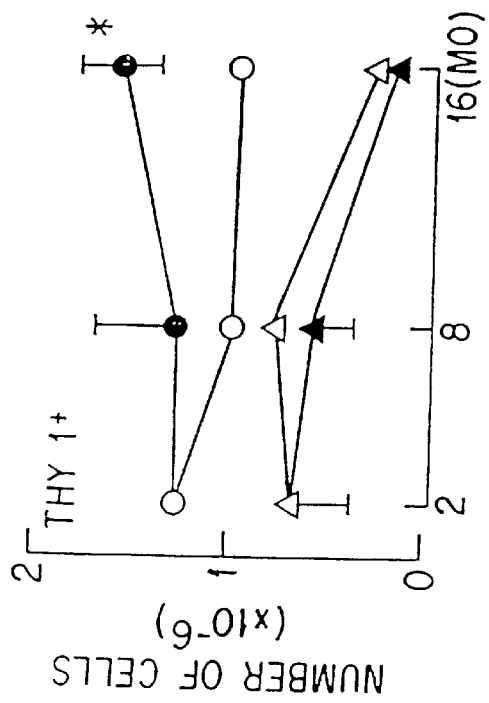
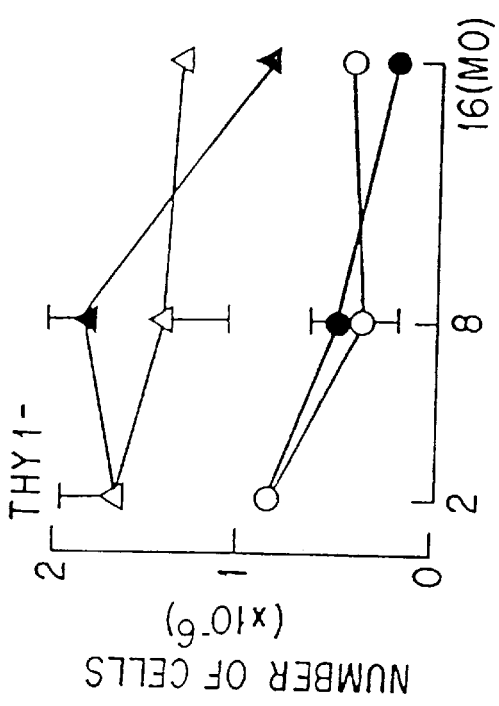
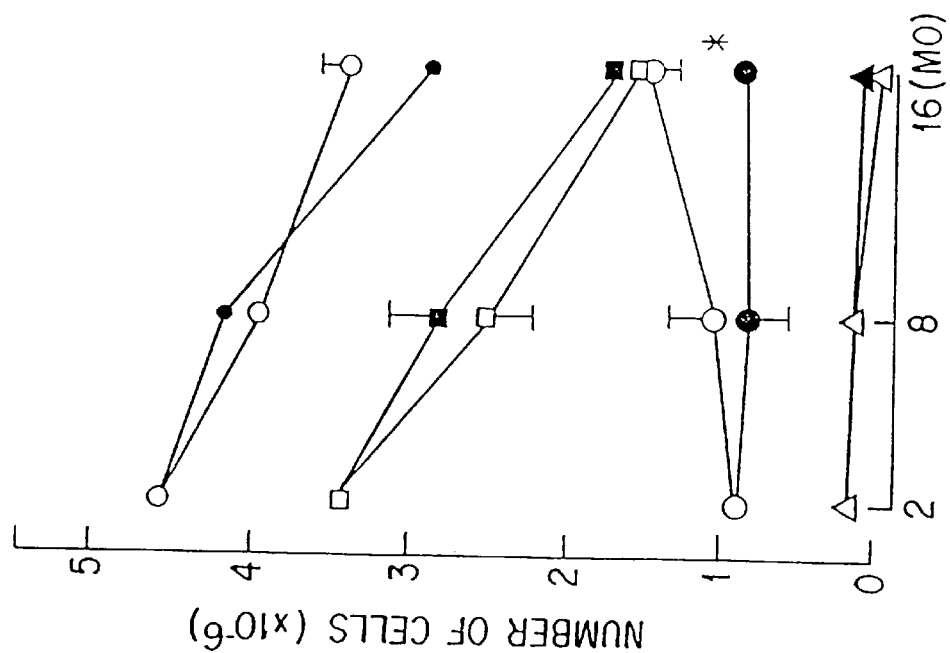

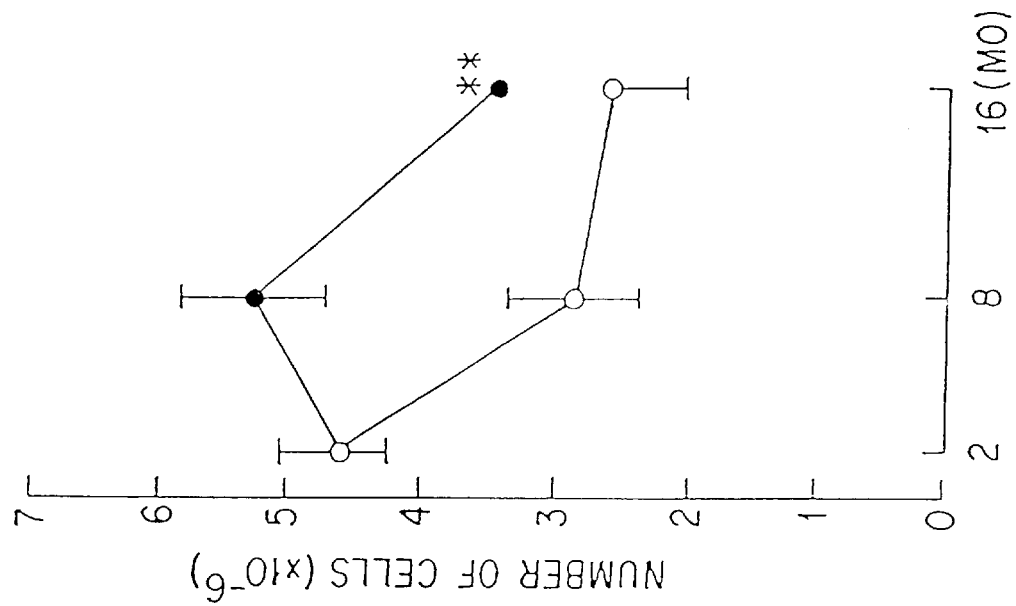
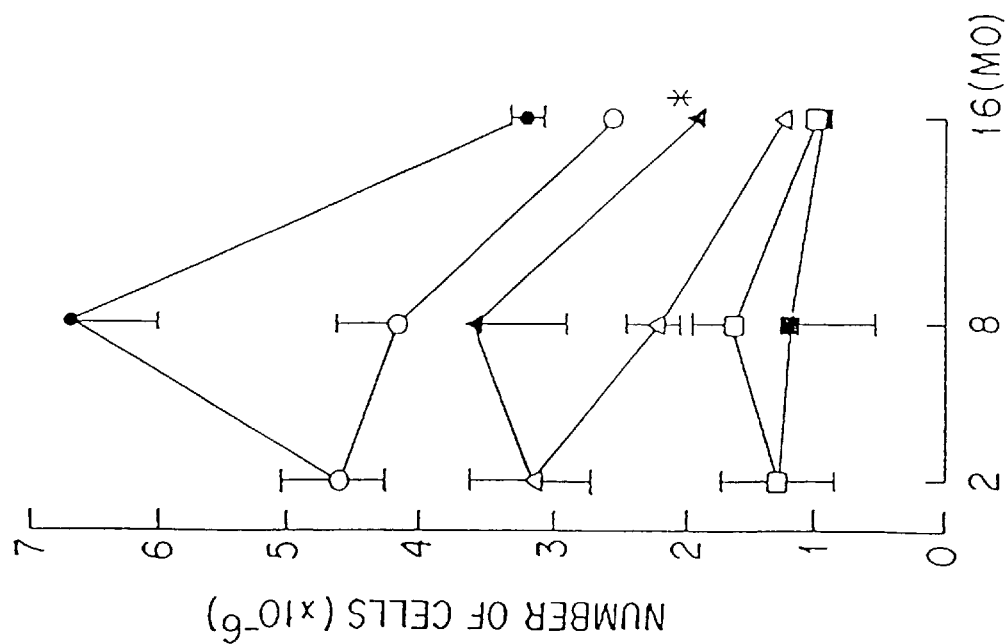
FIG. 6B
FIG. 6A

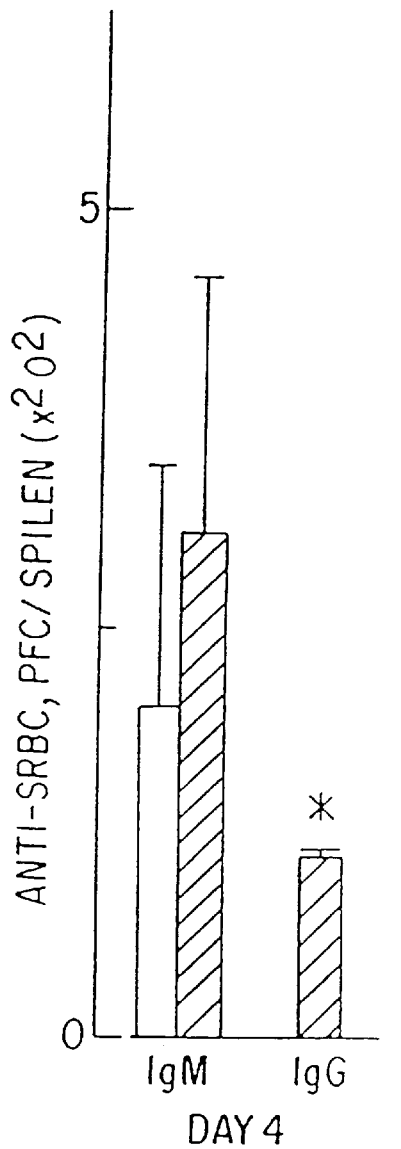
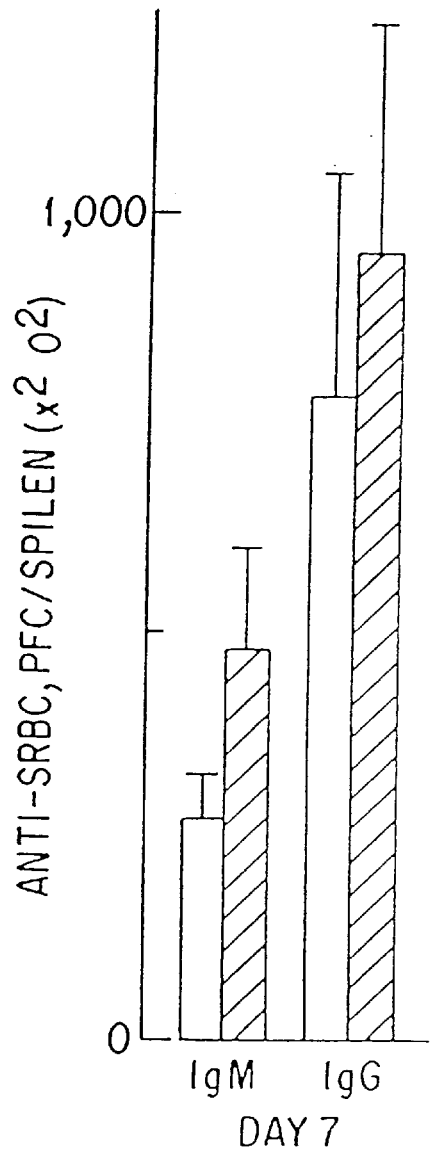
FIG. 10A
FIG. 10B

USE OF HYPERIMMUNE MILK TO PREVENT SUPPRESSION OF T-LYMPHOCYTE PRODUCTION

This application is a continuation of application Ser. No. 08/053,253, filed Apr. 28, 1993, abandoned, which is a continuation of 07/899,719, filed Jun. 16, 1992, abandoned.

FIELD OF THE INVENTION

The present invention relates to the use of hyperimmune milk for the prevention of suppression of T-lymphocyte function associated with the aging process, and thereby the retardation of immunological senescence or the aging process.

BACKGROUND OF THE INVENTION

Aging is characterized by a decline of the potential to adapt to environmental stresses. There is some evidence that aging in individuals is marked by a decline in normal immune cell functions (Makinodan et al., *Adv. Immunol.* 29:287–330 (1980); Wade et al., *Adv. Immunol.* 36:143–188 (1984)) and that the decline is due to decrease and changes of the heterogenous lymphoid cell population. (Bocci, V., *Biol. Rev,* 56:68 (1981). Clinical manifestations include increased incidence of infections, tumors, autoimmune and immune complex diseases. (Bocci, V., *Biol. Rev,* 56:68 (1981). The immune system deteriorates with aging as shown by decreases in the thymic lymphatic mass (Hirokawa et al., *Clin. Immunol. & Immunopathol.* 24:251–262 (1982)); the proliferative response of spleen cells to mitogenic or alloantigenic stimulation (Chandra, R. K., *Immunol.* 67:141–147 (1989); Adler et al., *J. Immunol.* 107:1357–1362 (1971)) and a decrease in the frequency of occurrence of anti-sheep erythrocyte (SRBC antibody in the spleen after immunization with SRBC (Price et al., *J. Immunol.* 108:413–417 (1972)). This effect of age is termed immunological senescence. The above noted changes in immunological functions associated with aging, predispose the subject to the onset of various undesired medical conditions, including autoimmune diseases, cancers, and life-threatening infections (Wade et al., *Adv. Immunol.* 36:143–188 (1984)).

Dietary manipulation (Chandra, R. K., *Immunol.* 77:141–147 (1989); Kubo et al., *J. Nutr.* 114:1884–1899 (1984); Gabrielsen et al., *Nature* 264:439–440 (1976)) and cell grafting (Hirokawa et al., *Clin. Immunol. & Immunopathol.* 24:251–262 (1982); Price et al., *J. Immunol.* 108:413–417 (1972)) have been proposed as treatments for the prevention or restoration of the above age-related changes in immunological functions. The disclosed methods for prevention of senescence in the immune system could help to decrease the life threatening risks associated with aging. However, dietary manipulation only slightly decreases life threatening risks associated with aging, while cell grafting is an experimental procedure requiring the use of immunosuppressive drugs to eliminate rejection of the graft. (Chandra, R. K., *Immunol.* 67:141–147 (1989)).

Wade et al. discusses the interaction between gut-associated lymphoid tissues (GALT) and the prevention of invasion of enteric bacteria (Wade et al., *Adv. Immunol.* 36:143–188 (1984)). GALT are composed of non-organized lymphoid components including intraepithelial lymphocytes (IEL) and lamina propia lymphocytes, and organized lymphoid components such as mesenteric lymph nodes (MLN) and Peyer's patches. The involvement of these cells in the defense against translocation of intestinal microflora in aged individuals, and/or immunological senescence in aged individuals is not clear. Rodney D. Berg reported that translocation of indigenous enteric bacteria from the GI tract does not occur in healthy, adult animals, but does occur in animals when (i) the permeability of the intestinal epithelium is altered, (ii) when there is abnormally high population levels of intestinal bacteria, and (iii) when the animal's immune system is compromised (Berg, Rodney D., *"Human & Intestinal Microflora in Health and Disease,"* Chap. 15:38–346 (1983)).

Currently, there are two known but problematic ways of protecting against the invasion of enteric bacteria. The first involves eliminating or reducing the number of intestinal pathogenic bacteria. Mastromarino et al. report that antibiotic administration significantly protects from the invasion of bacteria (Mastromarino et al., *Radiat. Res.* 68:329–338 (1976)). However, antibiotic administration also increases the susceptibility of a host to colonization by antibiotic resistant pathogens. This colonization in turn causes senile indigenous infectious disease. Further, Berg reports that the "indiscriminate use of oral antibiotics may disrupt the intestinal bacterial ecology, promoting bacterial translocation and placing patients at even greater risk for opportunistic infections" (Berg, Rodney D., *"Human Intestinal Microflora in Health and Disease,"* Chap. 15:342 (1983)). A second way to protect an individual from the invasion of enteric bacteria, that is, to protect from indigenous infection, is to specifically or nonspecifically augment the host's defense mechanisms against bacterial infection. Potent macrophage activators such as *Corynebacterium parvum* have been reported to decrease the rate of translocation of intestinal *Escherichia coli* in mice (Yoshikai et al., *Microbiol. Immunol.* 27:273–282 (1983)). Bovine milk immunoglobulin has also been reported to be effective in the prevention of enterotoxin *E. coli* or rotavius infections (Tacket et al., *N. Engl. J. Med.* 318:1240–1243 (1988); Hilpert et al., *J. Infect. Dis.* 156:158–166 (1987)).

SUMMARY OF THE INVENTION

The invention relates to the use of hyperimmune milk derived from milk producing animals hyperimmunized with bacterial antigens including intestinal bacteria. Administration of the present hyperimmune milk effectively prevents the decline of immunological functions observed in aging or immunocompromised animals and ameliorates or prevents the translocation of indigenous enteric bacteria from the GI tract of immunocompromised or aged animals, thereby treating or preventing indigenous infection. More specifically, the present hyperimmune milk when administered to an animal in an amount sufficient to effectively prevent translocation of indigenous enteric bacteria across the intestinal tract of compromised animals, delays the onset of, lowers the rate of, or restores the declining immune functions of, aging or otherwise immunocompromised animals.

The present inventors have now established that administration of hyperimmune milk derived from milk producing animals such as cows hyperimmunized with bacterial antigens, including intestinal bacteria such as *E. coli, S. typhimurium* and *S. dysenteriae,* effectively decreases the level of anti-intestinal-bacterial antibodies in the serum of aged or immunocompromised animals, such as aged mice. That is, the present hyperimmune milk prevents the translocation of enteric bacteria from the GI tract to the serum of an aged or immunocompromised animal. Further, the inventors have discovered that administration of such hyperimmune milk protects against the age associated decline of the proliferative response of GALT and spleen cells to stimulation by foreign antigens. That is, the present inventors have established that the use of hyperimmune milk protects against the decline of immunological functions associated with physiological aging and especially immunological senescence. Further, the present inventors have established that the administration of hyperimmune milk prevents infections caused by the translocation of indigenous bacteria from the gastrointestinal tract of immunocompromised or aged animals.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 5A–5C illustrates FACS analysis of cell surface markers on GALT cells. IEL and MLN cells were stained with Fluoresceinisothiocyanate (FITC)-anti-CD3 monoclonal antibody (Mab), PE-anti-CD4 Mab and biotin-anti-CD8 Mab, before addition of streptavidin-DuoCHROME. Triple-color analysis of CD4 and CD8 surface markers in CD3$^+$ cells was performed with using FACScan equipped FACSCAN Research Software. Others were stained with FITC-anti-C β (α/β (TcR)) (the Beta subunit constant region of α/β T-cell receptor) Mab or FITC-anti-C δ (γ/δ TcR) Mab (the Delta subunit constant region of γ/δ T-cell receptor), before addition of biotin-Thy1 and streptavidin-PE. FIGS. 5A–5C show the Cell kinetics of IEL subsets. Each point was calculated as total cell count×percentage of the cells with and/or without a cell surface markers; ○, CD3$^+$; △, CD4$^+$CD8$^-$; □, CD4$^-$CD8$^+$; ○, CD4–CD8– in IEL from mice given control milk (n=6) in Panel I. ○, αβ-bearing T cells; △, γδ-bearing T cells from mice given hyperimmune milk (n=6). ●, αβ-bearing T cells; ▲, γδ-bearing T cells from mice given hyperimmune milk (n=6) in Panel II. Each point and vertical bar represent $\bar{\chi}$ and SD. *Statistical difference was p<0.025 from a group given control milk.

FIGS. 6A–6C Cell kinetics of MLN cell subsets. FACS analysis as in FIGS. 5A–5C. Cell surface markers are indicated as same symbols represented in FIG. (5). Statistical difference were at *p<0.005 and **p<0.025 from a group given control milk.

FIG. 8 Mitogen response of MLN cells. ○, control milk (n=6); ●, hyperimmune milk (n=6). Each point and vertical bar represent $\bar{\chi}$ and SD. *Statistical difference was at *p<0.025 from a group given control milk.

FIG. 9 Mixed leukocyte reaction of MLN cells. △, control milk (n=6); ▲, hyperimmune milk (n=6). Each point and vertical bar represent $\bar{\chi}$ and SD. *Statistical difference was at p<0.05 from a group given control milk.

FIGS. 10A–10B illustrates numbers of plaque-formed cells to SRBC in the spleen. Mice (age, 8 mo.) were injected intraperitoneally with 1×10$^5$ SRBC. The mice were tested on day 4 and 7 after immunization. □, control milk; ■, hyperimmune milk. Each point and vertical bar represent $\bar{\chi}$ and SD. Statistical difference was at p<0.001 from a group given control milk.

DEFINITIONS

Figure 1:
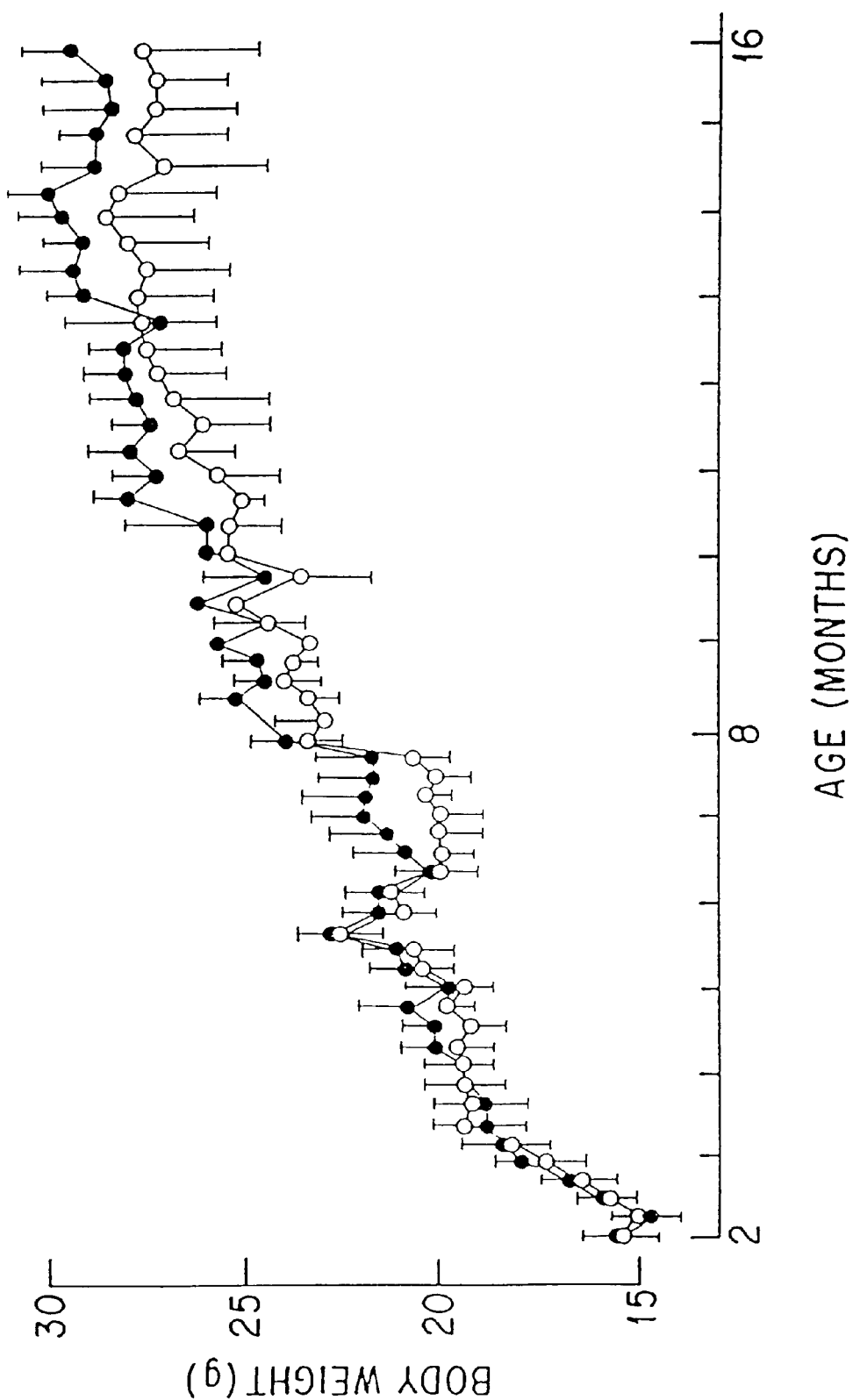
FIG. 1 illustrates a body weight curve. C57BL/6 mice, 2 mo. of age, were fed on two kinds of diets (120 g/kg body weight/day); ○, control milk; ●, hyperimmune milk; for 16 mo. Each point and vertical bar represent $\chi$ and SD (n=20). Body weight at any time points showed no statistical difference between two groups in Student's t-test.

By the term "hyperimmune milk" is intended, for the purpose of this invention, milk obtained from milk-producing animals maintained in a hyperimmune state, the details for hyperimmunization being described in greater detail below. Such milk may be in liquid or powder form and may include, for example, a skim milk form.

By the term "normal milk" or "control milk" is intended for the purpose of this invention, milk that is obtained from milk-producing animals by conventional means and dairy practices. Such milk, may be in liquid or powder form and includes, for example, skim milk powder obtained from Stolle Milk Biologics International (SMBI; Cincinnati, Ohio).

By the term "milk-producing animal" is intended, for the purpose of this invention, mammals that produce milk in commercially feasible quantities, preferably cows, sheep and goats, more preferably dairy cows of the genus Bos (bovid), particularly those breeds giving the highest yields of milk, such as Holstein.

By the term "administer" is intended, for the purpose of this invention, any method of treating a subject with a substance, such as orally.

By the term "treating" is intended, for the purposes of this invention, that the symptoms of the disorder and/or origin of the disorder be prevented, ameliorated or completely eliminated.

By the term "bacterial antigen" is intended, for the purpose of this invention, a preparation of live or killed bacterial cells or any component derived from bacterial cells, or from genes of bacterial origin.

By the term "microencapsulated form" is intended, for the purpose of this invention, polymeric microparticles encapsulating one or more bacterial antigens for administration to milk-producing animals.

By the term "animal" is intended, for the purpose of this invention, any living creature that is subject to immune function decline associated with aging, including for example, humans, farm animals, domestic animals, animals for use in research, and zoological garden animals.

By the term "indigenous infection" is intended, for the purpose of this invention, any blood or systemic bacterial infection resulting from the translocation of indigenous enteric bacteria (bacteria present in the animals gastrointestinal tract) from the gastrointestinal tract to other organs, tissue, blood, etc. Animals susceptible to such infections include those that are immunocompromised, i.e., suffer from diseases such as leukemia; aged animals; etc. Such indigenous infections can be prevented in animals including geriatric patients and immunocompromised patients by prophylactic treatment with hyperimmune milk.

By the term "immunological aging" is intended, for the purpose of this invention, a condition characterized by immunological senescence and especially in the decline of immune functions including, for example, any or all of decreased thymus T-cell counts; decreased mitogen response and mixed lymphocyte culture reaction of spleen and mesenteric lymph node cells; increased translocation of the number of bacteria or bacterial antigens from the gastrointestinal tract as shown by the presence of an increased number of antibodies to intestinal bacteria in the serum; decreased thymic lymphatic mass; decreased proliferative response of spleen cells to mitogenic or alloantigenic stimulation; decreased frequency of occurrence of anti-sheep erythrocyte (SRBC) antibody in the spleen after immunization with SRBC; and increased serum level of autoantibodies, for example, anti-ssDNA autoantibodies.

By the term "immunocompromised" animal or individual is intended for the purpose of this invention, an animal or human of any age suffering from a condition, for example, Acquired Immune Deficiency Syndrome (AIDS), which condition causes a decline in normal immune cell functions, i.e., the condition causes immunological aging of the animal or human.

DETAILED DESCRIPTION OF THE PREFERRED EMBODIMENTS

The present invention is directed toward the use of hyperimmune milk to prevent the decline of immunological functions associated with physiological aging and especially immunological senescence. Specifically, hyperimmune milk is administered to an animal in an amount sufficient to prevent the decline of immunological functions associated with aging and the decline of immunological functions observed in immunocompromised animals. More specifically, hyperimmune milk is administered in an amount sufficient to delay the onset of, lower the rate of, or restore the declining immune functions of aging or otherwise immunocompromised animals. The present invention is further directed toward preventing infections caused by the translocation of enteric bacteria, especially in immunocompromised or aged individuals.

The present invention is based in part on the discovery that when a milk-producing animal such as a bovid is brought to a state of hyperimmunization with a vaccine containing intestinal bacteria, the animal will produce milk, which contains supranormal levels of IgG against intestinal bacteria. Oral administration of this hyperimmune milk suppresses the decline of immunological functions associated with advanced physiological age and/or immune senescence and/or decline observed in an immunocompromised animal. By the term "supranormal" is intended levels in excess of that found in milk from non-hyperimmunized animals.

Hyperimmune milk is milk obtained from cows hyperimmunized against a variety of intestinal bacterial antigens, for example see Table 2. Hyperimmune milk is processed under thermo-regulation to maintain antibody activity. Hyperimmune milk is pasteurized using a low temperature pasteurization step at a range of 161° F. to 167° F. with a dwell time of 15–19 seconds, preferably at a temperature range of 163° F. to 165° F. with a dwell time of 16–18 seconds, and more preferably, a pasteurization temperature of 164° F. with a dwell time of 17 seconds. The pasteurization step is followed by a low temperature evaporation step at a temperature range of 100° F. to 110° F., preferably 103° F. to 107° F., and more preferably at 105° F. When the hyperimmune milk in the evaporation stage achieves a total solids content of at least 40% solids, the milk is spray dried utilizing a low temperature spray drying step with temperatures of 354° F. to 394° F., preferably from 364° F. to 384° F., and more preferably 374° F. The outlet temperature during spray drying ranges from 170° F. to 200° F., preferably from 180° F. to 190° F., more preferably at 185° F. The nutritional composition of hyperimmune milk is the same as that of control milk (Golay et al., *Am. J. Clin. Nutr.* 52:1014–1019 (1990)). The concentration of IgG, and the antibody activity of IgG against human intestinal bacteria (Table 2) is significantly higher in hyperimmune milk than in control milk.

a. Process for Producing Hyperimmune Milk

The hyperimmunized state may be achieved by administering an initial immunization sufficient to provoke an immune response and antibody production, followed by periodic boosters with sufficiently high doses of specific antigens. The preferred dosage of booster should be equal to or greater than 50% of the dosage necessary to produce primary immunization of the bovid. Thus, there is a threshold booster dosage below which the properties are not produced in the milk, even though the cow is in what normally would be called an immune state. In order to achieve the requisite hyperimmune state, it is essential to test the hyperimmune milk after a first series of booster administrations. If the beneficial factors are not present in the milk, additional boosters of high dosage are administered until the properties appear in the milk.

In summary, one process of producing the hyperimmune milk comprises the following steps: (1) antigen selection (intestinal bacteria, intestinal bacterial antigens and especially human intestinal bacteria or antigenic extractions thereof); (2) primary immunization of the milk producing animal, and especially the bovoid; (3) testing the serum to confirm sensitivity the primary induction; (4) hyperimmunization with boosters of appropriate dosage; and optionally, (5) testing the milk for protective properties; (6) collecting the milk from the hyperimmune bovid; and optionally (7) processing the milk.

Step 1: Any intestinal antigens or combination of intestinal antigens may be employed. The critical point in this step is that the intestinal antigen(s) must be capable, not only of inducing immune and hyperimmune states in the milk-producing animal, but also of producing supranormal levels of IgG against intestinal bacteria in the hyperimmune milk. One preferred vaccine is a mixture of polyvalent bacterial antigens, referred to as Series 100 vaccine, described in detail in Example 2.

Step 2: The antigen(s) of Step 1 can be administered to the milk-producing animal in any method that causes sensitization. In one method, a vaccine composed of antigen derived from $1 \times 10^6$ to $1 \times 10^{20}$, preferably $10^8$ to $10^{10}$, most preferably $2 \times 10^8$, heat-killed bacteria is administered by intramuscular injection. However, other methods such as intravenous injection, intraperitoneal injection, rectal suppository, or oral administration may be used.

Step 3: It is necessary to determine whether or not the milk-producing animal has become sensitive to the intestinal-bacteria antigen. There are a number of methods known to those skilled in the art of immunology to test for sensitivity (*Methods in Immunology and Immunochemistry*, William, C. A., and Chase, W. M., Academic Press, New York, vols. 1–5 (1975)). The preferred method is to use a polyvalent vaccine comprising multiple intestinal-bacteria species as the antigen and to test for the presence of agglutinating antibodies in the serum of the animal before and after challenge with the vaccine. The appearance of milk antibodies after immunization with the vaccine indicates sensitivity; at this point it is possible to proceed to step 4.

Step 4: This involves the induction and maintenance of the hyperimmune state in the sensitized animal. This is accomplished by repeated booster administration at fixed time intervals of the same polyvalent vaccine that was used to achieve the primary sensitization. A two-week booster interval is optimal for polyvalent bacterial antigens. However, it is necessary to ensure that the animal does not pass from a hyperimmune state to a state of immune tolerance to the antigen.

In a preferred embodiment, hyperimmunization of the milk-producing animal may be achieved by a single administration of microencapsulated vaccine, prepared as described in detail in Example 2. The advantage of the controlled release form of hyperimmunization is that the constant exposure to the antigen ensures that the animal remains in the hyperimmune state.

In an alternative embodiment, it is also possible to combine different immunization procedures, e.g., simultaneously administering microencapsulated and liquid antigen, or intramuscular injection for primary immunization, and booster doses by oral administration or parenteral administration by microencapsulation means. Many different combinations of primary and hyperimmunization are known to those skilled in the art.

Step 5: It is necessary to test the milk for protective effect. This can be accomplished by any known research technique that tests the effects of either the hyperimmune milk or products derived therefrom upon immune function.

Step 6: This involves the collection and processing of the milk. The milk can be collected by conventional methods. Further, the milk can be processed. Such processing can be by conventional methods. For example, the milk can be defatted to produce skim milk.

The hyperimmune milk of the present invention may be orally administered alone in a powder or liquid form or may be provided in a composition. These compositions can be administered in any amount or concentration that prevents the suppression of T-lymphocyte function or prevents immunological aging; or delay the onset of, lower the rate of, or restore declining immune functions.

Solid dosage forms of the hyperimmune milk of the invention for oral administration include capsules, tablets, pills, powders and granules. In such solid dosage forms the active compound is admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents. Tablets and pills can additionally be prepared with an enteric coating.

Liquid dosage forms for oral administration include pharmaceutically acceptable emulsions, including the milk itself, and solutions, suspensions, syrups and elixirs containing inert diluents commonly used in the pharmaceutical art. Besides inert diluents, such compositions can also include adjuvants, such as wetting agents, emulsifying and suspending agents, and sweetening.

The dosage of active ingredients in the composition of this invention may be varied; however it is necessary that the amount of the active ingredient shall be such that a suitable dosage form is obtained. The selected dosage form depends upon the desired therapeutic effect, on the route of the administration and on the duration of the treatment. Further, the selected dosage form can be easily determined by one of ordinary skill in the art.

Preferably, hyperimmune milk is orally administered to an animal in the form of a skim milk powder in an amount sufficient to prevent the suppression of T-lymphocyte function or to prevent immunological aging. A suitable dosage range is from about 1 g/kg body weight per day to about 200 g/kg body weight per day, preferably from about 50 g/kg body weight per day to about 150 g/kg body weight per day, and more preferably about 98 g/kg body weight per day. The preferred frequency of daily dosing is from 1–4 doses per day, preferably 2 doses per day. The preferred length of treatment is for life.

Hyperimmune milk may be administered in other dry forms such as whole milk powder, bulk protein concentrate powders or whey protein concentrate powders. A suitable dosage range for whole milk powder is similar to the dosage range specified for skim milk powder. A suitable dosage range for milk protein concentrate powder and whey protein concentrate powder is from about 0.1 grams per kilogram body weight per day to about 20 grams per kilogram body weight per day, preferably from about 5 grams per kilogram per body weight per day to about 15 grams, per kilogram body weight per day and more preferably, about 9.8 grams per kilogram body weight per day. The hyperimmune milk may also be administered in a liquid form such as whole milk, skim milk, milk protein concentrate, whey protein concentrate or as a component of another liquid for administration. A suitable dosage range for liquid hyperimmune milk products is 0.1 milliliter per kilogram body weight per day to about 200 milliliters per kilogram body weight per day, preferably from about 1 milliliter per kilogram body weight per day to about 50 milliliters per kilogram body weight per day, and more preferably about 25 milliliters per kilogram body weight per day. The preferred frequency of daily dosing is from 1 to 4 doses per day, preferably 2 doses per day. A preferred length of treatment is for life.

Administration dosage and frequency, and length of treatment will depend on the age and general health condition of the animal or patient, and the species, taking into consideration the possibility of side effects. The optimization of dosage, frequency and length of treatment can be accomplished by one of ordinary skill in the art. Administration will also be dependent on concurrent treatment with other drugs and patients' tolerance of the administered drug.

Bacteria or bacteria antigens thereof, suitable for use in the vaccine of the present invention include intestinal bacteria of humans or other animals. Such suitable bacteria include, for example, the following:

(1)* members of the family Enterobacteriaceae, including for example:

Shigella including *S. dysenteriae* (American Type Culture Collection (ATCC) deposit Nos: 13313, 11835; human; 27345, 29027, 29028; animal: 27346/chimpanzee); *S. flexneri* (ATCC Nos.: 29903; human: 25929 and 25875); *S. boydii* (ATCC Nos.: 8700; human: 25930); *S. sonnei* (ATCC Nos.: 29930; human: 25931, 29029, 29030 and 29031);

Escherichia including *E. coli* (ATCC Nos.: 26, 11775; human: 9339, 9546, 9980, 11698, 11699, e11775, 12036, 23510–23512, 23514, 23515, 23519, 23520–23522, 23524, 23526–23529, 23977, 23530–23534, 23978, 23980–23983, 29552 and 23985; animal: cow/4350, 4351, 23540, 23541, and 23543);

Edwardsiella including *E. hoshinae* (ATCC No.: animal: puffin/33379); and *E. tarda* (ATCC Nos.: human: 15947, 15469, 23657–23712 and 23837);

Salmonella including *S. paratyphi-A* (ATCC Nos.: 9150, 9281, 12176 and 11511); *S. schottmuelleri* (ATCC No. 8759); *S. typhimurim* (ATCC Nos.: 13311; animal: cow/14028); *S. choleraesuis* (ATCC Nos.: e13312, 7001); *S. enteritidis* (ATCC Nos.: 4931 and 13076); *S. gallinarum* (ATCC No.: 9184); S.sp. (ATCC No.: 29890) including serotypes: montevideo (ATCC No.: 8387), newport (ATCC Nos.: 6962, 27869), anatum (ATCC No.: 9270), newington (ATCC No.: 29628), heidelberg (ATCC No.: 8326), saintpaul (ATCC No.: 9712), potsdam (ATCC No.: 25957), zwickau (ATCC No.: 15805) and javiana (ATCC No.: 10721);

Arizona including *A. hinshawii* (*Salmonella arizonae*) (ATCC No.: e13314);

Citrobacter including *C. freundii* (ATCC Nos.: 8090; human: 6750, 29219–29222, and 33128; animal: livestock/29935); and *C. diversus* (ATCC Nos.: 27156; human: 25409, 29224, and 29225);

Klebsiella including *K. pneumoniae* (ATCC Nos.: 9590, 13883; human: 20916, 20917, 33495, 29642; animal: cow/4352, beaver/4727);

Enterobacter (formally "Aerobacter") including *E. cloacae* (ATCC Nos.: human: e13047, 29005, 29006, 10699, and 29893); *E. aerogenes* (ATCC Nos.: 884; human: e13048, 15038, 29010, 29751 and 29940); *E. agglomerans* (ATCC Nos.: human: 27155, 27988, 27984, 27987, 29001, 29002, 27998, 27981, 27993, 27991 and 27989); *E. hafiniae alvei* (same as *Hafnia alvei*) (ATCC Nos.: 13337, 9760, 11604, 23280,25927, human: 29926 and 29927);

Serratia including *S. marcescens* (ATCC Nos.: 13880; human: 9103, 25179, 27137, 29021, 29022, and 29937, animal: ape/4002, lizard/6065); *S. liquefaciens* (ATCC Nos.: 27592; 11367, e14460, 14461, 19323, animal: dairy products/25641–25643); and *S. rubidaea* (ATCC Nos.: 27593, human: 29023);

Proteus including *P. mirabilis* (ATCC Nos.: 29906; 4675, 9240, 9921, 12453, 14153, 14273, 15290, 15363, 21100, 21635, and 21718; human: 4630, 7002, 25933, 29852, 29854–29856); *P. morganii; P. vulgaris* (ATCC Nos.: e13315; human: 8427, 27972, 27973, 33420, 6898);

Providencia including *P. rettgeri* (ATCC Nos.: 29944; 9918, 9919, 14505, 21118, 31052; human: 9250, 25932); *P. alcalifaciens* (ATCC Nos.: human: 9886, 13159, 25828, 27970, 27971 and 29945); *P. stuartii* (ATTC Nos.: 29914; human: 25825, 25826, 25827 and 29851);

Yersinia including *Y. enterocolitica* (ATCC Nos.: human: 9610, 23715, 27729; animal: monkey/29913) and *Y. pseudotuberculosis* (ATCC Nos.: 29833; human: 29910, animal: 6905, 13979, 13980, 27802);

(2)* members of the family Vibrionaceae including for example: Vibrio including *V. parahaemolyticus* (ATCC No.: 17802); and *Vibrio succinogens;*

(3)* Enterococci including for example:

Streptococci including *Strep. faecalis* (ATCC Nos.: e19433; 27275, 27274, 27276, human: 6569, 33074, 27274, animal: cow/27959, 27332); *Strep. faaecium* (ATCC Nos.: 19434; human: 6056, 12755, 27270, 27273); *Strep. bovis* (ATCC Nos.: animal: cow/15315, 15352, 27960, 33317); *Strep. agalactiae* (ATCC Nos.: 13813; human: 624; animal: cow/27956, 27541, 12927, 12928, 7077, 4768); *Strep. anginosus; Strep. avium; Strep. cremoris* (ATCC Nos.: 19257, 9596; 9625); *Strep. equismilius* (Atcc No.: 9542); *Strep. lactis* (ATCC Nos.: 19435, 7962, 7963, 27861; animal: dairy products/e11454, 21053, 29146); *Strep. mitior; Strep. mitis* (ATCC Nos.: human: 903, 6249, 15909–1514); *Strep. mutans* (ATCC Nos.: 25175; human: 27607, 27947, 31341); *Strep. salivarius* (ATCC Nos.: 13419; human: 31067, 27945, 25975, 9758); *Strep. sanguis* (ATCC Nos.: human: 10556–10558, 29667, 29668); *Strep. equinus* (ATCC No.: 9812); Strep. Durans (see *Strep. faecium*); *Strep. pyogenes* (ATCC Nos.: 8671, 10389, 12347, 12349, 12972, 12357, 10403, 12344; human: 7958, 19615, 21059, 21547, 11434–11436, 25663, 10782); *Strep. pneumoniae* (ATCC Nos.: 6301–6312, e6303, 9163, 10813, 11733, 12213, 27336, 6314–6332, 8333–8340, 10341–10359, 10361–10373, 10015); *Strep. constallatus* (ATCC Nos.: human: 27513, 27823); *Strep. hansenii* (ATCC No.: human: 27752(; *Strep. intermedius* (ATCC No.: 27335) and *Strep. morbillorium* (ATCC Nos.: human: 27527, 27824);

Staphylococci including *Staph. aureus* (ATCC Nos.: 11631; human: 12600, 13150, 9996, 14458, 19636, 21915, 21915, 27217, 4012, animal: cow/27543, 29740); *Staph. albus; Staph. epidermidis* (ATCC Nos.: human: e155, 14990, 10875);

(4)* Lactobacilli including *L. acidophilus* (ATCC Nos.: e4356, 314, 332, 521, 832, 4355, 4357, 4796, 4962, 9224, 11975, human: 33197, 33200, animal: pig/33198, chicken/33199); *L. brevis* (ATCC Nos.: human: 14869, 11577); *L. buchneri* (ATCC Nos.: 4005; human: 11579, 12935, 12936); *L. casei* (ATCC Nos.: e393, 7469, human: 27216, 21052, 11578, 11582, 15008, 4646, animal: dairy products/25599, 25598, 334); *L. catenaforme* (ATCC No.: human: 25536); *L. crispatus; L. fermentum* (ATCC Nos.: 14931; human: 23271, 23272, 11976, 14932); *L. helveticus* (ATCC Nos.: 15009, 8018, 10386); *L. lactis* (ATCC Nos.: dairy products: 12315, 21051); *L. leichmannii* (ATCC Nos.: 4797, 7830); *L. minutus* (ATCC No.: human: 33267); *L. planareum* (ATCC Nos.: 14917, 4008; human: 11974); *L. rogosae* (ATCC No.: human: 27753); *L. ruminis* (ATCC Nos.: human: 25644; animal: 2778–27782); *L. salivarius* (ATCC Nos.: 11742, 11741, 29602);

(5)* Campylobacter including *C. fetus var intestinalis* (ATCC Nos.: human: 33246–33249, 33293) and *C. fetus var jejuni* (ATCC Nos.: human: 29428, 33250–33253, 33291, 33292);

(6)* Aeromonas including *A. hydrophilia* (ATCC Nos.: 7966; animal: frog/e9071, fish/19570); and *A. shigelloides* (ATCC Nos.: 14029, 14030);

(7)* members of the family Bacteroidaceae including genera Bacteroides, Fusobacterium and Leptrotrichioe, including:

Bacteroides including *B. amytophilus; B. asaccharolyticus* (ATCC Nos.: 25260; human: 27067); *B. capillosus* (ATCC No.: human: 29799); *B. coagulans* (ATCC No.: human: 29798); *B. distasonis* (ATCC No.: 8503); *B. eggerthii* (ATCC No.: human: 27754); *B. fragilis* (ATCC Nos.: human: 23745, 25285, 29768, 29771); *B. hypermegas* (ATCC No.: chicken/25560); *B. melaninogenicus* (ATCC Nos.: human: 15032, 15033, 25261, 25611, 15930, 25845, 33184, 33185; animal: bovine/29147); *B. multiacidus* (ATCC Nos.: human: 27723, 27772, animal: pig/27724); *B. oralis* (ATCC Nos.: human: 33269, 33321, 33322); *B. ovatus* (ATCC No.: 8483); *B. pneumonsintes; B. praeacutus* (ATCC No.: human: 25539); *B. putredinis* (ATCC Nos.: human: 27908, 29800); *B. ruminicola* (ATCC Nos.: human: 27518; animal: bovine/19188–19189); *B. splanchinicus* (ATCC No.: human: 29572); *B. thetaiotaomicron* (ATCC Nos.: human: 12290, 29148, 29741–29742); *B. succinogenes* (ATCC No.: bovine/19169); *B. uniformis* (ATCC No.: 8492); *B. ureolyticus; B. vulgatus* (ATCC Nos.: 8482; human: 29327);

Fusobacterium including *F. gonidiaformans* (ATCC No.: 25563); *FJ. mortiferum* (ATCC Nos. 9817; human: 25557); *F. naviforme* F(ATCC No.: human: 25832); *F. necrogenes* (ATCC No.: duck/25556); *F. necrophorum* (ATCC Nos.: 25286; sheep/27852); *F. nucleatum* (ATCC Nos.: 10953, 23726; human: 25586); *F. plauti* (ATCC No.: 29863); *F. prausnitzii* (ATCC No.: human: 27766); *F. russi* (ATCC No.: cat/25583); *F. symbiosum; F. varium* (ATCC Nos.: 8501, 27725);

Leptotrichia including *L. buccalis* (ATCC Nos.: human: 14201, 19616, 23471, 23472);

(8)* Pseudomanads, including *P. aeruginosa* (ATCC Nos.: e10145, 142, 7700–7701; human: 9027, 10197, 14203–14213, 15152, 15692,17434, 17648, 17657, 17933–17934, 19142–19143, 19429, 19660, 21726, 23268, 23992,23994, 23996–23999, 25000–25004, 25010, 27312–23718, 29260, 33347, 33467–33468, 33494,19582, 10752); *P. maltophilia* (ATCC Nos.: 17806; human: 13636, 13637, 15099,17445, 17672, 17674, 17676, 17677); P. sp. (ATCC Nos.: 19151, 27109; human: 23713);

(9)* Acinetobacter;

(10)* Moraxella including *M. lacunata* (ATCC Nos.: human: e17967, 11748, 17970, 17972; animal: guinea-pig/17956); *M. osloensis* (ATCC Nos.: human: 19976, 17974, 19954–19956, 19965); *M. nonliquefaciens* (ATCC Nos.: human: 19975, 17954, 17975); *M. phenylpyruvica* (ATCC Nos.: human: 17958, 23333–23335);

(11)* Alcaligenes including *A. faecalis* (ATCC Nos.: e8750; human: 13138, 15554, 19018);

(12)* Achromobacter including *A. xylosoxidans* (ATCC Nos.: human: 27061–27063);

(13)* Eubacteria including *E. aerofaciens* (ATCC Nos.: human: 25986, 29738); *E. alactolyticum* (ATCC Nos.: human: 23263, 23264, 19301); *E. biforme* (ATCC No.: human: 27806); *E. budayi* (ATCC No.: 25541); *E. cellulosolvens; E. combesii* (ATCC No.: 25545); *E. contortum* (ATCC No.: human: 25540); *E. cylindroides* (ATCC Nos.: human: 27528, 27803–27805); *E. dolichum* (ATCC Nos.: human: 29143–29144); *E. eligens; E. formicigenerans* (ATCC No.: human: 27755); *E. halii; E. lentum* (ATCC No.: human: 25559); *E. limosum* (ATCC Nos.: 8486, 10825); *E. moniliforme* (ATCC No.: human: 25546); *E. multiforme* (ATCC No.: human: 25546); *E. nitritogenes* (ATCC No.: 25547); *E. ramulus* (ATTC No.: human: 29099); *E. rectale; E. ruminatium* (ATCC No.: bovine/17233); *E. saburream* (ATCC Nos.: human: 33271, 33318, 33319); *E. siraeum* (ATCC No.: human: 29066); *E. tenue* (ATCC No.: human: 25553); *E. tortuosum* (ATCC No.: turkey/25548); *E. ventriosum* (ATCC No.: 27560);

(14)* Peptococcaceae including:

Peptococcus including *P. asaccharolyticus* (ATCC Nos.: 14963; human: 29743); *P. magnus* (ATCC Nos.: 14955, 15794; human: 14956, 29328); *P. prevotii* (ATCC Nos.: human: 9321, 14952); *P. saccharolyiticus* (ATCC No.: human: 14953); *P. variabilis* (see *P. magnus*);

Peptostreptococcus including *P. anaerobius* (ATCC No.: 27337); *P. micros* (ATCC No.: human: 33270); *P. parvulus; P. productus* (ATCC No.: human: 27340);

Ruminococcus including *R. albus* (ATCC No.: bovine/27211); *R. bromii* (ATCC No.: human: 27255); *R. flavefaciens; R. lactaris* (ATCC No.: human: 29176); *R. obeum* (ATCC No.: human: 29174); *R. torques* (ATCC No.: human: 27756);

Sarcina including *Sarcina ventriculi* (ATCC Nos.: 29068, 29069);

(15)* Bifidobacteria including *B. adolescentis* (ATCC Nos.: human: 15703–15706); *B. angulatum* (ATCC Nos.: 27535, 27669, 27670, 27671); *B. bifidum* (ATCC Nos.: human: 11146, 11147, 11863, 15696, 29521); *B. breve* (ATCC Nos.: human: 15698–15701); *B. catenulatum* (ATCC Nos.: human: 27539, 27675–27677); *B. cornutum; B. dentium* (ATCC Nos.: human: 15423–15424, 27534, 27678–27680); *B. eriksonii; B. infantis* (ATCC Nos.: human: 15697, 15702, 17930, 25962, 27920); *B. longum* (ATCC Nos.: human: 15707–15708); and *B. pseudolongum* (ATCC Nos.: animal: swine/25526, bovine/25864–25865);

(16)* Clostridia including *C. acetobutylicum* (ATCC Nos.: 824,3625, 4259, 8529, 10132); *C. aminovalericum* (ATCC No.: 13725); *C. aurantibutyricum* (ATCC No.: 17777); *C. barati; C. barkeri* (ATCC No.: 25849); *C. bejerinkii* (ATCC Nos.: 858, 6014, 11914, 14949, 14950, 17778, 17795, 25752); *C. bifermentans* (ATCC Nos.: 638, 971;5, 17836–17840, 19299); *C. butyricum* (ATCC Nos.: human: 25799; animal: pig/19398); *C. cadaveris* (ATCC Nos.: 9687, 25783); *C. carnis* (ATCC No.: 25777); *C. celatum* (ATCC No.: human: 27791); *C. cellobioparum* (ATCC No.: cattle/15832); *C. chauvoei* (ATCC Nos.: animal: bovine/10092, 19399; sheep/11957–11958); *C. clostridiiforme* (ATCC Nos.: 29084; animal: calf/25537); *C. cochlearium* (ATCC No.: 17787); *C. difficile* (ATCC Nos.: 9689, 17857–17858); *C. fallax* (ATCC No.: 19400); *C. felsineum* (ATCC Nos.: 13160, 17788–17789); *C. ghoni* (ATCC No.: 25757); *C. glycolicum* (ATCC Nos.: 14880, 29797); *C. haemolyticum* (ATCC Nos.: 9650, 9652); *C. indolis* (ATCC No.: 25771); *C. innocum* (ATCC No.: human: 14501); *C. irregularis* (ATCC No.: 25756); *C. lentoputrescens* (ATCC No.: 17794); *C. limosum* (ATCC No.: 25620); *C. leptum* (ATCC No.: human: 29065); *C. malenominatum* (ATCC Nos.: 17793, 25776); *C. mangenoti* (ATCC No.: 25761); *C. nexile* (ATCC No.: human: 27757); *C. oceanicum* (ATCC Nos.: 25647–25649); *C. oroticum; C. paraputrificum* (ATCC Nos.: 17796, 17864, 25780); *C. pasteurianum* (ATCC Nos.: 6013, 7040–7041); *C. perfringens ATCC Nos.: human: 12918–12920, 19574; animal: chicken/14810, lamb/10388, 3629, 3627, 3626); *C. plagarum; C. pseudotetanicum; C. putrefaciens* (ATCC No.: 25786); *C. sartagofarmum* (ATCC No.: 25778); *C. septicum* (ATCC Nos.: 6008–6009, 8053–8054, 8065;, 11424, 12464); *C. sordelii* (ATCC No.: 9714); *C. sphenoides* (ATCC Nos.: 3560, 19403); *C. sporosphaeroides* (ATCC No.: 25781); *C. subterminale* (ATCC Nos.: 25774, 29748); and *C. tertium* (ATCC Nos.: 14573, 19405);

(17)* *Acidaminococcus fermentans* (ATCC Nos.: pig gut/ 25085–25088);

(18)* Coprococcus including *C. eutactus* (ATCC No.: human 27759); *C. catus* (ATCC No.: human: 27761); *C. comes* (ATCC No.: human: 27758);

(19)* *Gemiger formicilis* (ATCC No.: 27749);

(20)* *Megasphera elsdenii* (ATCC Nos.: 17752–17753; animal: pig/25940);

(21)* Actinomyces including *A. naeslundii* (ATCC Nos.: human: 12104, 19039, 27038–27040); and *A. odontolyiticus* (ATCC Nos.: human: 17929, 17982, 29323);

(22)* *Arachnia propionica* (ATCC Nos.: human: 14157, 29324–29326);

(23)* *Lachnospira multiporus* (ATCC No.: bovine/ 19027);

(24)* Propionobacterium including *P. acnes* (ATCC Nos.: human: 29399, 33179, 6919, 6921–6923, 11827, 11828); *P. avidum* (ATCC No.: 25577); *P. granulosum* (ATCC No.: 25564); and *P. jensenii* (ATCC Nos.: 4867–4871, 4964, 14073);

(25)* *Veillonella parvula* (ATCC No.: human: 10790);

(26)* *Butyrivibrio fibrisolvens* (ATCC Nos.: bovine/ 19171, 27208);

(27)* Desulfotomaculum including *D. nigrificans* (ATCC Nos.: 19998, 7946, 19858); *D. ruminis* (ATCC No.: sheep/ 23193); *D. orientis* (ATCC No.: 19365);

(28)* *Desulfomanas pigra;*

(29)* *Oscillospira guillermondii;*

(30)* *Selenomonas ruminatium* (ATCC No.: bovine/ 19205);

(31)* *Sucinimonal amylolytica;*

(33)* *Succinivibrio dextrinosolvens* (ATCC No.: cow/ 19716);

(34)* *Aerococcus viridans* (ATCC Nos.: 10400, 11563, 29503, 29838);

(35)* Bacillus including *B. cereus* (ATCC Nos: e14579, 2, 246, 4342, 6464, 7004, 7039, 9139, 9818; sheep/12480); *B. subtilis* (ATCC Nos.: e6051, 82, 465, 4529);

(36)* Corynebacterium species (ATCC Nos: 6931, 6933, 6935–6938, 9736–9744; human: 13959–13962, 15927, 17892; animal: mouse/11035; bovine/9739–9741);

(37)* Micrococcus species (ATCC Nos.: 9274, 12084, 13553–13555, 21829);

(38) Diplococcus including *Diplococcus pneumoniae* (ATCC No.: 6303);

(39) Haemophilus including hemophilus influenza (ATCC No.: 9333);

(40)* Nocardia species (ATCC Nos: 12288, 13635, 14558–14559, 15074, 19170, 19534, 21145, 21147, 21430, 21519, 27942, 29100, 29664, 31233, 31280,31281, 31319); and (41)* Pediococcus species (ATCC No.: 8459).

*Davis et. al., *Microbiology*, 3rd. ed., Chap. 31–33, Harper & Row, (1980); Drasar, B. S., *Role of the Gut Flora in Toxicity and Cancer*, Academic Press, pp. 34–36, (1988); American Type Culture Collection, Rockville, Md., Catalogue of strains I, 15th ed. pp57–250 (1982); all of which are hereby incorporated by reference.

Any bacteria present in the intestinal tract of humans or animals, is suitable for use in the vaccine of the present invention. The selection of suitable bacteria from the above listed bacteria is within the knowledge of one of ordinary skill in the art. The selection of other bacteria not expressly set forth above is also within the knowledge of one of ordinary skill in the art.

b. Testing of the Effects of Hyperimmune Milk on an Animal

The effects of the present hyperimmune milk can be tested as follows:

(i) Diet

The animal to be tested can be fed any general nutrition diet along with the hyperimmune milk of the present invention. The term "general nutrition diet" refers to any diet which would be used to maintain an individual of the particular species of interest in good health. For example, mice would normally be fed a commercially available mouse chow available from a number of suppliers.

The hyperimmune milk can be fed in any form, but is preferably fed in the form of a skim milk powder. The skim milk powder is fed in an amount sufficient to effectively prevent, delay, or restore declining immune functions, as well as in an amount sufficient to effectively prevent infection caused by the translocation of enteric bacteria in geriatric or immunocompromised animals. The hyperimmune skim milk powder of the present invention can be administered in an amount of from about 1 to about 200 g/kg body weight per day, preferably from about 50 to about 150 g/kg body weight per day, more preferably the hyperimmune skim milk powder can be administered in an amount of about 98 g/kg body weight/day.

When the animal to be tested is a mouse, a preferred diet comprises the following: skim milk powder in an amount of from about 70 to about 90 weight percent; glycerol in an amount of from about 4 to 7 weight percent; safflower oil in an amount of from about 2 to 5 weight percent; a mineral mixture such as AIN-76 in an amount of from about 3 to 8 weight percent; a vitamin mixture such as AIN-76 in an amount of from about 1 to 3 weight percent; methionine in an amount of from about 1 to 3 weight percent; and coline bitartrate in an amount of from about 0.1 to about 4.5 weight percent, of the mixture.

Suitable control diets include any nutritional diet wherein the hyperimmune milk of the present invention is replaced with control milk.

(ii) Milk Samples

The hyperimmune milk of the present invention is processed under thermo-regulation, as previously described, to maintain antibody activity. The hyperimmune milk can be tested by any generally known means to ensure that antibody activity has been maintained. Methods for testing hyperimmune milk to insure that antibody activity is present, include, for example, ELISA.

(iii) Determination of Bacteria

To determine the effect of hyperimmune milk against enteric bacteria, pieces of the animal's small intestine, large intestine or cecum can be homogenized in any appropriate media, including, for example, heart infusion broth (Difco Laboratories, Detroit, Mich.) by any well known method, on ice to maintain bacteria viability and to suppress artificial growth of bacteria. Dilutions of the homogenized intestine can then be plated on any suitable media, including, for example, MacConkey's agar, in petri dishes and incubated for a suitable time, for example, 18–48 hours, at 37° C., at which time the number of colonies can be counted to determine the number of Enterobacteriaceae in the intestinal tract.

The hyperimmune milk of the present invention results in a lowered number of Enterobacteriaceae in the large intestine and cecum as compared with the number observed in animals fed a control milk diet.

(iv) Estimation of the Level of Invasion of Bacteria Translocating from the Gastrointestinal Tract To estimate the level of invasion of bacteria translocating from the gastrointestinal tract of the animal, the serum level of antibodies to enteric mucosal bacteria can be measured prior to and after the administration of hyperimmune milk.

To determine the serum level of antibodies to enteric bacteria, any method known in the art can be utilized, including, for example, enzyme linked immunosorbent assay (ELISA).

The present hyperimmune milk results in decreased levels of antibodies to intestinal bacteria as compared to the levels observed in animals receiving a control milk diet.

(v) Protective Effect of Hyperimmune Milk on Age-Related Decline of Immunological Functions of GALT Cells To determine the effect of hyperimmune milk on immunological functions of GALT cells, IEL populations are first examined.

Intestinal intraepithelial lymphocytes (IEL) can be isolated according to any method known in the art, including, for example, the modified method of the procedure described in Goodman et al. (*J. Exp. Med.* 170:1569–1581 (1989).

The hyperimmune milk of the present invention, in IEL, inhibited the increase of $CD4^-CD8^-$ cells associated with normal aging as compared with cell counts observed in animals fed a control milk diet. Also, in IEL, the hyperimmune milk of the present invention results in increased $Thy1^+\alpha\beta$ TcR-bearing cells, as compared to the cell number observed in animals fed a control milk diet. The hyperimmune milk of the present invention, in MLN, decreased the number of $CD4^+$ cells as compared to the number observed in animals fed a control milk diet.

Thymic, spleen, mesenteric lymph node, and IEL cells, can be analyzed using well known flow cytofluorometric analysis methods. For example, fresh cells can be stained using monoclonal antibodies, for example, as set forth in Example 1. The stained samples can then be analyzed, for example, with a single-beam flow cytometer (FACScan, Becton Dickinson). Forward and side angle light scatter can be used to exclude dead and aggregated cells. The data collected can then be analyzed using known methods; for example, the data can be analyzed with Consort 30 research software (Becton Dickinson) in the case of double-color analysis, and with FACScan research software in the case of triple-color analysis.

(vi) Enhancement of Cytolytic Activity

IEL represent a unique $CD3^+$ T cell population which has the ability to exhibit cytolytic activity and plays an important role in local immune-defense against the invasion of bacteria and virus.

The redirected cytolytic activity of IEL in an animal given hyperimmune milk as compared to an animal fed a control milk diet, to tumor cells, including, for example, P815 target cells in the presence of anti-CD3 monoclonal antibody, can be assayed by known techniques, including, for example, the redirected cytolytic assay disclosed in Goodman et al. (*Nature* 333:855–857 (1988)). The present hyperimmune milk results in enhanced cytolytic activity against tumor cells as compared with activity observed in animals fed a control milk diet. Further, the activity maintained is at a level approximately equal to that observed in young animals.

(vii) Mitogenic Stimulation

In MLN cells, the proliferative response to mitogens decreases with an animal's age. The present hyperimmune milk results in the suppression of age-related decline of the responsiveness of MLN cells to mitogens, as compared with the responsiveness observed in animals fed a control milk diet.

MLN cells can be assayed for responsiveness to mitogens using any commonly known method. For example, see Example 1.

The present hyperimmune milk also significantly protects an animal from a decline of proliferative response to alloantigens.

(viii) Protective Effect of Hyperimmune Milk on Age-Related Decline of Immune Response After Systemic Immunization To evaluate the whole body effect of hyperimmune milk on age-related decline of immune function, a PFC assay can be performed. Specifically, after immunization with sheep red blood cells (SRBC), animals can be assayed for plaque-forming cells in the spleen to SRBC. Such assay can be carried out by any well known method, including, for example, the method set forth in Example 1, i.e., a modification of the Jerne-Norden slide method. The present hyperimmune milk prevents the decline in the ability of spleen cells to produce anti-sheep erythrocyte antibody.

(ix) Serum Level of Anti-DNA Antibodies in Aged Mice

To evaluate the effect of hyperimmune milk on age-related immune dysfunction, the production of anti-ssDNA autoantibodies in the sera from young and old animals can be examined. For example, the sera from young and old mice can be examined. More specifically, the sera from mice from about 7 to 9 months of age can be compared with the sera of mice from about 15 to 17 months of age. The presence of autoantibodies in the sera increases with aging, as previously reported (Cato et al., *Aging Immunol. Inf. Dis.* 1:177–190 (1988)).

The present hyperimmune milk suppresses an increase in the serum level of anti-DNA autoantibodies as compared with the serum level observed in animals fed a control milk diet. Autoantibodies can be detected utilizing any well known technique including, for example, ELISA, RIA or immunoblotting.

Having now described the invention in general terms, the same will be further described by reference to certain specific examples that are provided herein for purposes of explanation only, and are not intended to be limiting unless otherwise specified.

EXAMPLES

Example 1

Effects of Hyperimmune Milk on Immunological Functions a. Materials and Methods (i) Mice.

Female C57BL/6 mice, 6 weeks of age, were purchased from Japan SLC, Shizuoka. After pre-feeding for 2 weeks mice of each group were fed a hyperimmune or control skim milk diet (120 g/kg body weight/day) containing mixture of nutrients (Table 1) for 14 months. Mice were killed at 8 and 16 mo. of age and assays to determine immunological profile were performed.

TABLE 1

Composition of diet used

| Constituent | Weight % |
|---|---|
| Skim milk* | 81.5 |
| Glycerol | 5.5 |
| Safflower oil | 3.3 |
| AIN-76** | |
| Mineral mixture | 5.8 |
| Vitamin mixture | 1.7 |
| Methionine | 1.8 |
| Coline bitartrate | 0.3 |

*Two kinds of skim milk powders were supplied by SMBI. One was derived from cows after immunization with bacteria (Table 2) and was processed under thermoregulation to maintain antibody activity. The other was derived from unimmunized cows and was processed under standard conditions. Other ingredients were purchased from Kuroda, Fukuoka.
**Compositions of vitamins and minerals are as reported in Tacket et al., N. Engl. J. Med. 381: 1240–1243 (1988). Vitamins, coline, methionine, minerals, milk, oil and glycrol were mixed. The mix diets were kept at 4° C. The 120 g/kg body weight/day of diet were measured in an animal room and were put into mouse cages.

(ii) Milk samples.

The skim milk powder from cows hyper-immunized against a variety of human gut bacterial antigens (Table 2) and the control skim milk powder were provided by Stolle Milk Biologics International (SMBI; Cincinnati, Ohio). Hyperimmune milk was processed under thermo-regulation to maintain antibody activity. The nutritional composition of hyperimmune milk was the same as that of control milk (Golay et al., *Am. J. Clin. Nutr.* 52:1014–1019 (1990)). The concentration of IgG, and the antibody activity of against human gut bacteria (Table 2) were significantly higher in hyperimmune milk than in control milk.

TABLE 2

S-100 Bacteria List

| | Name | Media | Gram + or − | ATTC # |
|---|---|---|---|---|
| 1 | *Staph. aureus* | BHI | + | 11631 |
| 2 | *Staph. epidermidis* | BHI | + | 155 |
| 3 | *Strep. pyogenes*, A. Type 1 | APT | + | 8671 |
| 4 | *Strep. pyogenes*, A. Type 3 | APT | + | 10389 |
| 5 | *Strep. pyogenes*, A. Type 5 | APT | + | 12347 |
| 6 | *Strep. pyogenes*, A. Type 8 | APT | + | 12349 |
| 7 | *Strep. pyogenes*, A. Type 12 | APT | + | 11434 |
| 8 | *Strep. pyogenes*, A. Type 14 | APT | + | 12972 |
| 9 | *Strep. pyogenes*, A. Type 18 | APT | + | 12357 |
| 10 | *Strep. pyogenes*, A. Type 22 | APT | + | 10403 |
| 11 | *Aerobacter aerogenes* | BHI | − | 884 |
| 12 | *Escherichia coli* | BHI | − | 26 |
| 13 | *Salmonella enteritidis* | BHI | − | 13076 |
| 14 | *Pseudomonas aeruginosa* | BHI | − | 7700 |
| 15 | *Klebsiella pneumoniae* | BHI | − | 9590 |
| 16 | *Salmonella typhimurium* | BHI | − | 13311 |
| 17 | *Haemophilus influenzae* | BHI | − | 9333 |
| 18 | *Strep. mitis* | APT | + | 6249 |
| 19 | *Proteus vulgaris* | BHI | − | 13315 |
| 20 | *Shigella dysenteriae* | BHI | − | 11835 |
| 21 | *Strep. pneumoniae* | APT | + | 6303 |
| 22 | *Propionibacter acnes* (anaerobe) | actinomyces Broth | + | 11827 |
| 23 | *Strep. sanguis* | APT | + | 10556 |
| 24 | *Strep. salvarius* | APT | + | 13419 |
| 25 | *Strep. mutans* | BHI | + | 25175 |
| 26 | *Strep. agalactiae* | APT | + | 13813 |

(iii) Determination of bacteria.

Pieces of small intestine, large intestine and cecum were homogenized in heart infusion broth (Difco Laboratories, Detroit, Mich.) on ice to maintain tissue viability and to suppress artificial growth of bacteria. Dilutions of the homogenized organs were then plated on MacConkey's agar in petri dishes and incubated at 37° C. for 18–48 hr, at which time the number of colonies was counted.

(iv) ELISA

Enzyme linked immunosorbent assay (ELISA) was employed to determine the serum level of antibodies to enteric bacteria (Table 2) and autoantibodies to DNA. Briefly, for anti-bacteria antibody assay, 50 $\mu$L of heat killed bacteria (1.6 $\mu$g/mL; generously provided by SMBI; Table 2) in 0.1 mol/L borate buffer, pH 8.5 was put into 96-well EIA plates (Costar, Cambridge, Mass.). For the anti-DNA autoantibody assay, 50 $\mu$l of single strand DNA (10 $\mu$g/mL) was put into wells. Each plate was kept for coating at 4° C. overnight. Thereafter, the plates were blocked with a 10 g/L BSA solution and washed three times with 0.5 g/L Tween 20 phosphate buffered saline (PBS) solution to prevent nonspecific adherence. Thereafter, 50 $\mu$L dilutions of serum ($3^3$ fold dilutions with Tween/PBS solution) was put into each well. The plates were incubated for 2 hr at room temperature and then washed. Secondly, 50 $\mu$L of alkaline phosphatase-coupled goat anti-mouse IgG (1,000 fold dilutions with Tween/PBS, Tago, Burlingame, Calif.) was put into each well. The plates were kept for 2 hr at room temperature, and then washed four times. Lastly, development of the wells was initiated by the addition of 50 $\mu$L of chromogen (1 g/L p-nitrophenylphosphate, 100 g/L monoethanolamine, 1 g/L $MgCl_2$, pH 9.2) to each well. The development reaction was stopped with 3 mol/L NaOH. The resulting color was measured as absorbance at 405 nm with reference at 492 nm by using a microplate photometer(EAR 400; SLT, Salzburg).

(v) Purification of murine IEL.

Intestinal intraepithelial lymphocytes (IEL) were isolated according to a modified method of the procedure described previously in Goodman (Goodman et al., *J. Exp. Med* 170:1569–1581 (1989)). Briefly, the small intestines were cut into 5 mm pieces, and were then stirred at 37° C. in medium 199 (GIBCO, Grand Island, N.Y.) with the addition of 1 mM dithioerythritol (Sigma Chemical Co., St. Louis, Mo.). Mixtures of lymphocytes and epithelial cells were then centrifuged through a 30/67.5% Percol gradient (Petet et al., *Eur. J. Immunol.* 15:211–215 (1985); Ballas et al., *J. Immunol.* 138:1647–1852 (1987); Sontoni et al., *J. Immunol.* 134:2799–2807 (1985)). Cells at the interface were collected.

(vi) Flow cytofluorometric analysis.

Fresh thymic cells, spleen cells, mesenteric lymph node (MNL) cells and IEL were stained using monoclonal antibodies as follows: H57-597, anti-TcR$\beta$ chain (kindly provided by Dr. R. Kobo, National Jewish Center for Immunology and Respiratory Medicine, Denver, Colo.); CL3, anti-TcR $\gamma/\delta$ (PharMingen, San Diego, Calif.); 145-2C11, anti-CD3 $\epsilon$ chain (kindly provided by Dr. J. A. Bluestone, University of Chicago, Chicago, Ill.); biotin-conjugated anti-Thy 1.2 (Caltag, San Francisco, Calif.), biotin-conjugated anti-Lyt 2, and phycoerythrin-conjugated anti-L3T4 (both from Becton Dickinson). Other reagents were phycoerythrin-conjugated streptavidin and duoCHROME-conjugated streptavidin (both from Becton Dickinson). The stained samples were analyzed with a single-beam flow cytometer, FACScan (Becton Dickinson). Forward and side angle light scatter were used to exclude dead and aggregated cells. The data was analyzed with Consort 30 Research Software (Becton Dickinson) in the case of double-color analysis, and with the FACSCAN Research Software in the case of triple-color analysis.

(vii) Redirected cytolytic assay.

IEL were assayed for lytic activity against the Fc receptor+ DBA/2 mastocytoma P815 cells (Goodman et al., Nature 333:855–857 (1988)). Freshly isolated IEL were incubated in 96-well round bottom microtiter plates for 4 hr at 37° C. at a concentration of $10^5$ cells per well with $1.5 \times 10^3$ of $^{51}$Cr-sodium chromate-labeled P815 target cells that had been previously incubated with 1 μg/mL of a monoclonal antibody specific for the ε chain of the CD3 complex (2C11). Percent specific lysis was calculated as 100×[(cpm released with effectors)−(cpm released alone)]/[(cpm released by detergent)−(cpm released alone)]. Spontaneous release was less than 10%.

(viii) Mitogenic stimulation.

Mesenteric lymph node (MLN) cells were assayed for responsiveness to mitogens. Fresh MLN cells were cultured in 96-well plates for 68 hr at 37° C. at a concentration of $2.5 \times 10^5$ cells per well with 1 μL/mL of PHA-P (*Phaseolus vulgaris* agglutinin; Difco, Detroit, Mich.). [methyl-$^3$H] thymidine with 37 MBq was added into each well for an additional 4 hr of incubation. After harvesting cells, samples were counted by using the Beta-Plate System (Pharmacia, Uppsala, Sweden). The cultured samples having added thereto an equal volume of medium instead of mitogens, were used as the reference controls. Specific stimulation index (SI) was calculated as $(CPM_{exp})/(CPM_{ref})$.

(ix) Mixed leukocyte reaction.

MLN cells were assayed for responsiveness to allogeneic spleen cells. Fresh MLN cells were cultured in 96-well round bottom microtiter plates (Corning, N.Y.) for 68 hr at 37° C. at a concentration of $2.5 \times 10^5$ cells per well with allogeneic spleen cells which had been previously irradiated with 25 Gy. [methyl-$^3$H] thymidine with 37 MBq was added to each well and incubated for an additional 4 hours. The cells were then harvested and the cpm of the samples was determined. The cpm of samples cultured with syngeneic spleen cells from 1.5-mo.-old C57BL/6 mice instead of allogeneic cells from BALB/c mice was determined, and used as reference controls.

(x) PRC assay.

Sheep red blood cells (SRBC;Nippon Bio-Test Laboratories, Tokyo) were washed three times in medium (RPMI 1640; GIBCO) before use. To measure the primary response, mice were immunized intraperitoneally with $10^3$ SRBC. Four and seven days later, the mice were killed, and the spleens were removed. The spleen cells were assayed for plaque-forming cells (PFC) by a modification of the Jerne-Norden slide method. Briefly, fresh single cells from a spleen were suspended in 5 mL of medium. The SRBC pellet was suspended 6.5 fold in medium. Thereafter, 100 μL of SRBC suspension, 100 μL of guinea pig fresh serum and 20 μL of spleen cell suspension were respectively added into each tube on ice. The mixed suspensions were then put into Jerne-Norden slides. The slides after sealing with vaseline were incubated at 37° C. for 2 hr. The resulting PFC were counted.

(xi) Statistics.

The standard Student's t-test was employed to determine the significance of the difference between two groups.

Results (i) Dietary influence on body weight and cell populations of various lymphoid tissues.

Figure 2:
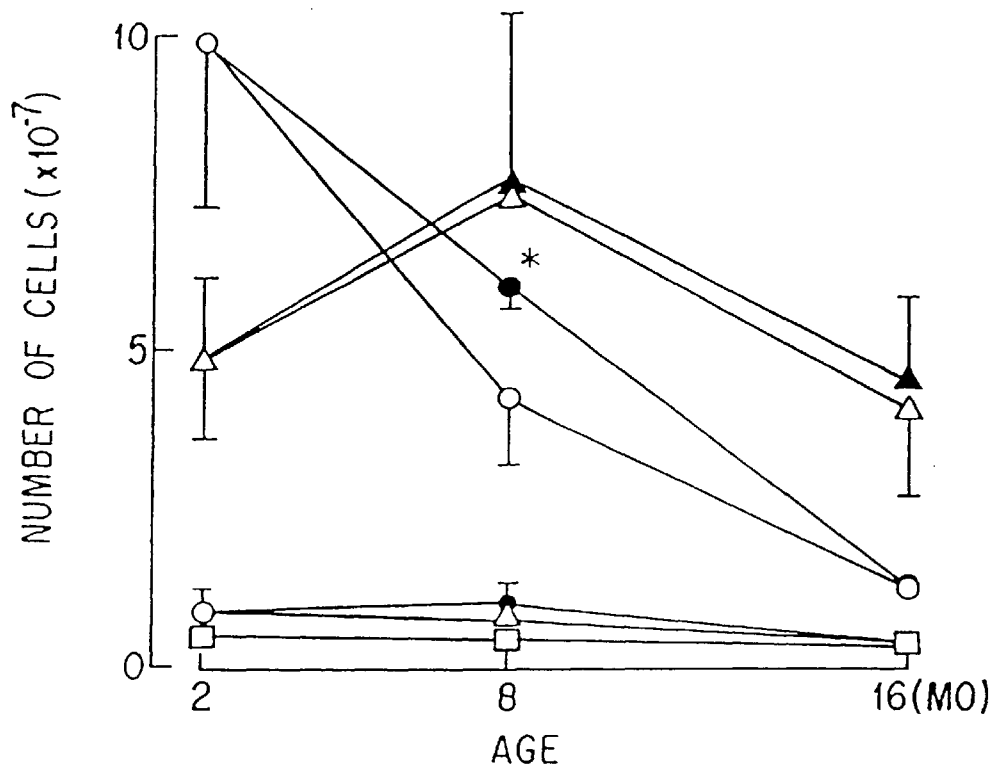
FIG. 2 illustrates the cell kinetics of various lymphoid tissues. Murine organs were sampled at 8 and 16 mo. of age. ○, thymus; △, spleen; □, MLN; ○, IEL, which were from mice given control milk (n=8). ●, thymus; ▲, spleen; ■, MLN; ○, IEL, which were from mice given hyperimmune milk (n=8). Each point and vertical bar represent $\bar{\chi}$ and SD. Statistical difference in a t-test was at p<0.005 from a group given control milk.

Before examination of the influence of oral administration of hyperimmune milk on immunological functions, the kinetics of body weight and cell numbers in various lymphoid tissues were first observed (FIG. 1). Body weight of both groups given hyperimmune milk or control milk increased gradually till 12 mo. of age. On the other hand, cell numbers in the thymus decreased with aging in both groups (FIG. 2). However, a decrease in thymocyte number at 8 mo. of age was prevented slightly but significantly (p<0.005) by hyperimmune milk. In contrast, cell numbers of spleen, MLN and IEL were much the same between both groups during the observation period.

(ii) Action of hyperimmune milk against enteric bacteria.

Figure 3:
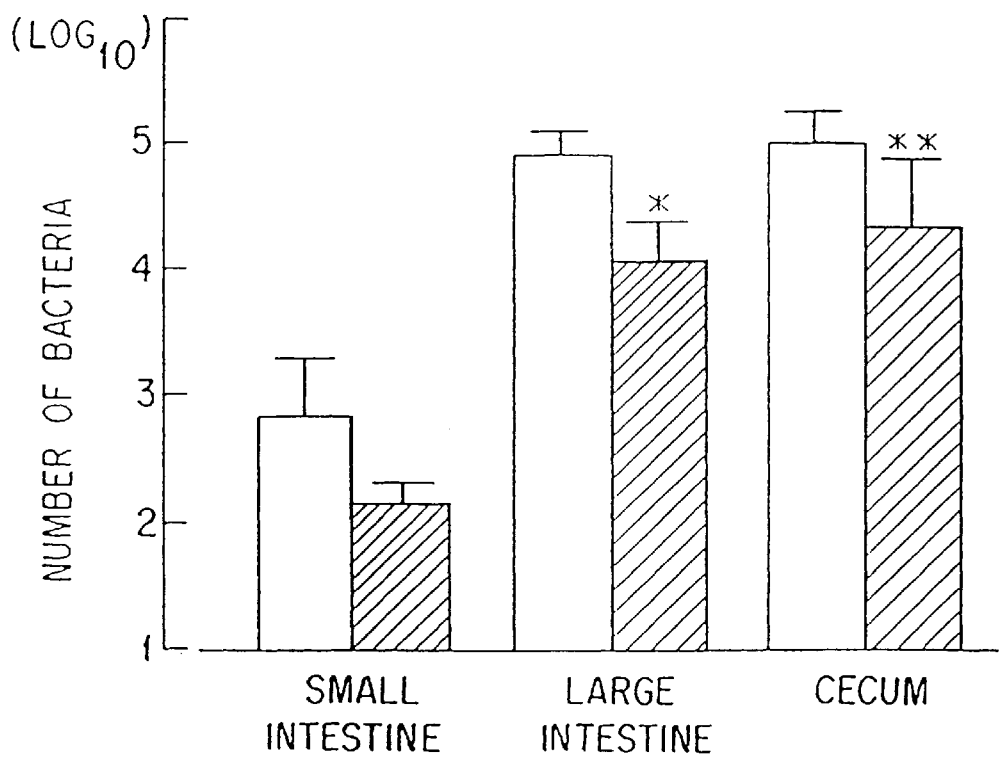
FIG. 3 illustrates the number of Enterobacteriaceae in the intestinal tract. Five individual mice (age, 8 mo.) from each group; □, control milk; ■, hyperimmune milk; were tested. Each point and vertical bar represent $\bar{\chi}$ and SD. Statistical difference were at *p<0.05 and **p<0.025 from a group given control milk.

To investigate the effects of administration of hyperimmune milk on intestinal microflora in aged mice, the number of Enterobacteriaceae in the intestinal tract were counted at middle age (8 mo.). As shown in FIG. 3, hyperimmune milk lowered the number of Enterobacteriaceae in the large intestine (p<0.05) and cecum (p<0.025) as compared with the number observed in mice given control milk. To estimate the level of the invasion of bacteria translocating from the gastrointestinal tract, the serum level of antibodies to mucosal bacteria (Table 2) at 8 and 16 mo. of age (FIG. 4) was measured. Hyperimmune milk decreased the level of antibodies to intestinal bacteria as compared to the levels observed in mice given control milk (p<0.005; age, 8 mo.).

(iii) Protective effect of hyperimmune milk on age-related decline of immunological functions of GALT cells.

To determine the influence of hyperimmune milk on immunological functions of GALT cells, IEL and MLN cell populations were examined. In IEL, as shown in FIGS. 5A–5C (I and II), CD4⁻CD8⁻ cells increased less as compared with that in mice given control milk. In MLN cells (FIGS. 6A–6B, CD4⁺ cells decreased at 16 mo. of age as compared with that in young mice. Hyperimmune milk inhibited the decrease in the number of CD4⁺ cells as compared to the number observed utilizing control milk (p<0.005).

Figure 7B:
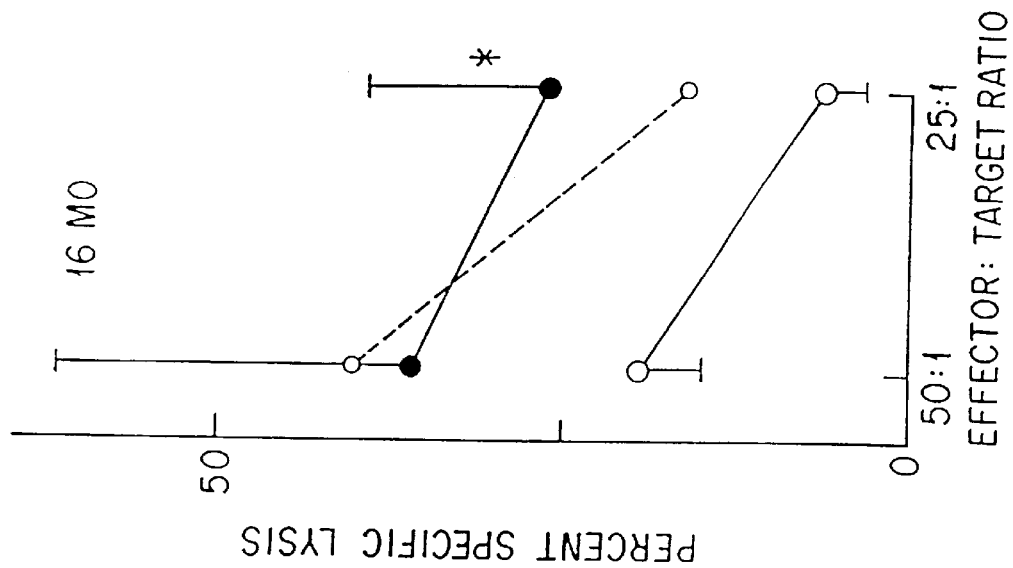
FIGS. 7A–7B illustrates a cytolytic assay of IEL. $^{51}$Cr-sodium chromate-labeled P815 tumor cells were used at a concentration of 1.5×10$^3$ cells per well in the presence of 1 μg/Ml of anti-CD3 Mab. Six individual mice from each group; ○, control milk; ●, hyperimmune milk; o, reference (age, 1.5 mo.). Each point and vertical bar represented $\bar{\chi}$ and SD. *Significant difference in a t-test was at p<0.1 from a group given control milk.
Figure 7A:
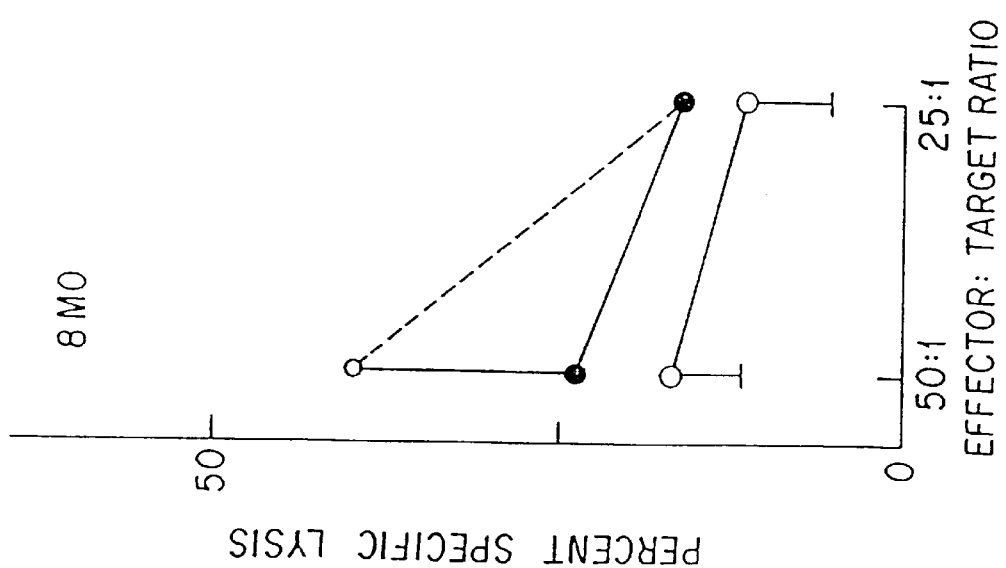
Figure 8:
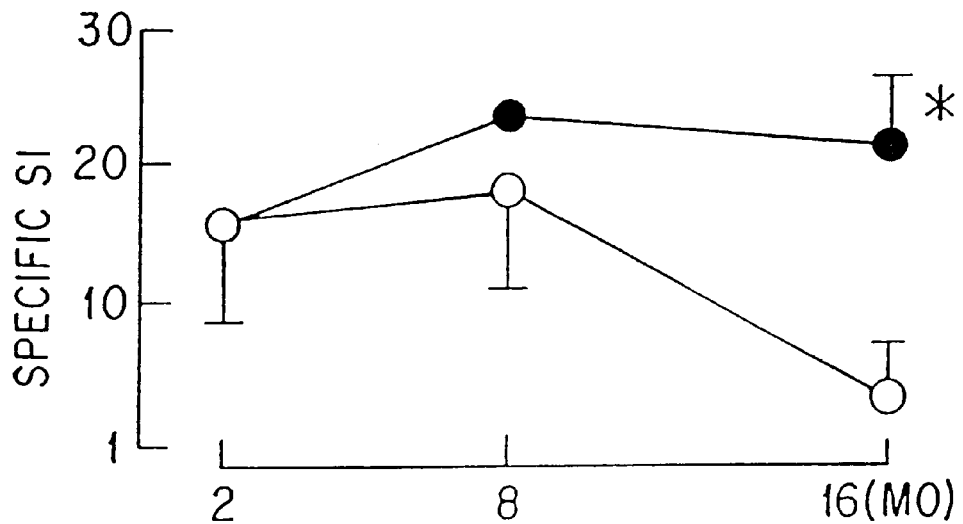
FIGS. 8 and 9 illustrates a proliferative responses of MLN cells to mitogen and alloantigen. The cells were cultured for 68 hr at 37° C. at a concentration of 5.0×10$^5$ cells per well with 2 μg/Ml of PHA or equal volume of spleen cells from BALB/c mice. [Methyl-$^3$H]-thymidine with 37 MBq was added into well for additional 4 hr incubation.
Figure 9:
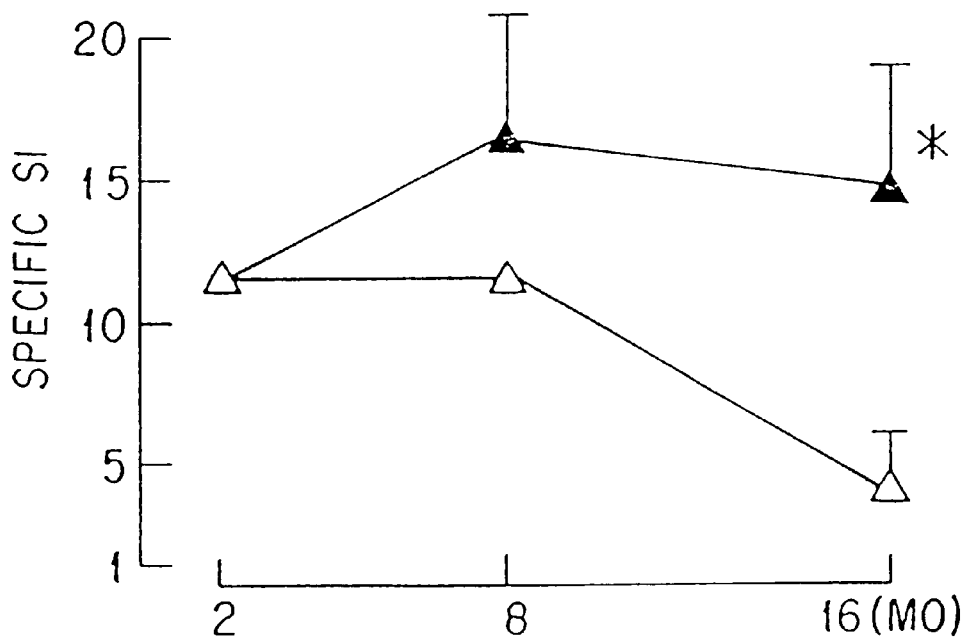

IEL represent a unique CD3⁺ T cell population which has the ability to exhibit cytolytic activity, and plays an important role in local immune-defense against the invasion of bacteria and virus (Janeway, A., Nature 333;804–806 (1988)). Therefore, the redirected cytolytic activity of IEL in mice given hyperimmune milk and control milk, to P815 target cells in the presence of anti-CD3 mAb, was assayed (FIGS. 7A–7B). Hyperimmune milk enhanced cytolytic activity against P815 tumor cells as compared with activity observed in mice given control milk (p<0.1), and maintained the activity at a level approximately equal to that observed in young mice (age, 2 mo.). In MLN cells, as shown in FIG. 8, the proliferative response to PHA (a kind of mitogen for T cells) decreased at 16 mo. of age. Hyperimmune milk suppressed the age-related decline of the responsiveness significantly as compared with the responsiveness observed in mice given control milk (p<0.005). Hyperimmune milk also significantly protected mice from a decline of proliferative response to alloantigen observed (spleen cells from BALB/c mice) with aging (p<0.025; FIG. 9.

(iv) Protective effect of hyperimmune milk on age-related decline of immune response after systemic immunization.

To further investigate the whole-body effect of hyperimmune milk on the age-related decline of immune function, a PFC assay was performed. On day 4 and 7 after immunization of 8-mo.-old mice with SRBC, the mice were assayed for plaque-forming cells in the spleen to SRBC (FIGS. 10A–10B). IgM-bearing cells appeared on day 4, at which time IgG-bearing cells were not detected in mice given control milk, whereas hyperimmune milk increased the number of IgG-bearing cells to a detectable level (p<0.001). The numbers of IgM-bearing and IgG-bearing cells on day 7 after immunization with SRBC showed no significant difference between mice given hyperimmune and control milk.

(v) Serum level of anti-DNA antibodies in aged mice.

To investigate the influence of hyperimmune milk on age-related immune dysfunction, the production of anti-ssDNA autoantibodies in the sera from 8 and 16 mo. old mice was examined (FIGS. 10A–10B). Autoantibodies arose with aging, consistent with previous reports (Kato et al., Aging Immunol. Inf. Dis. 1:177–190 (1988)). Hyperimmune milk suppressed an increase in the serum level of anti-DNA antibodies as compared with the serum level observed in mice given control milk ($p<0.1$; age, 16 mo.).

Figure 4:
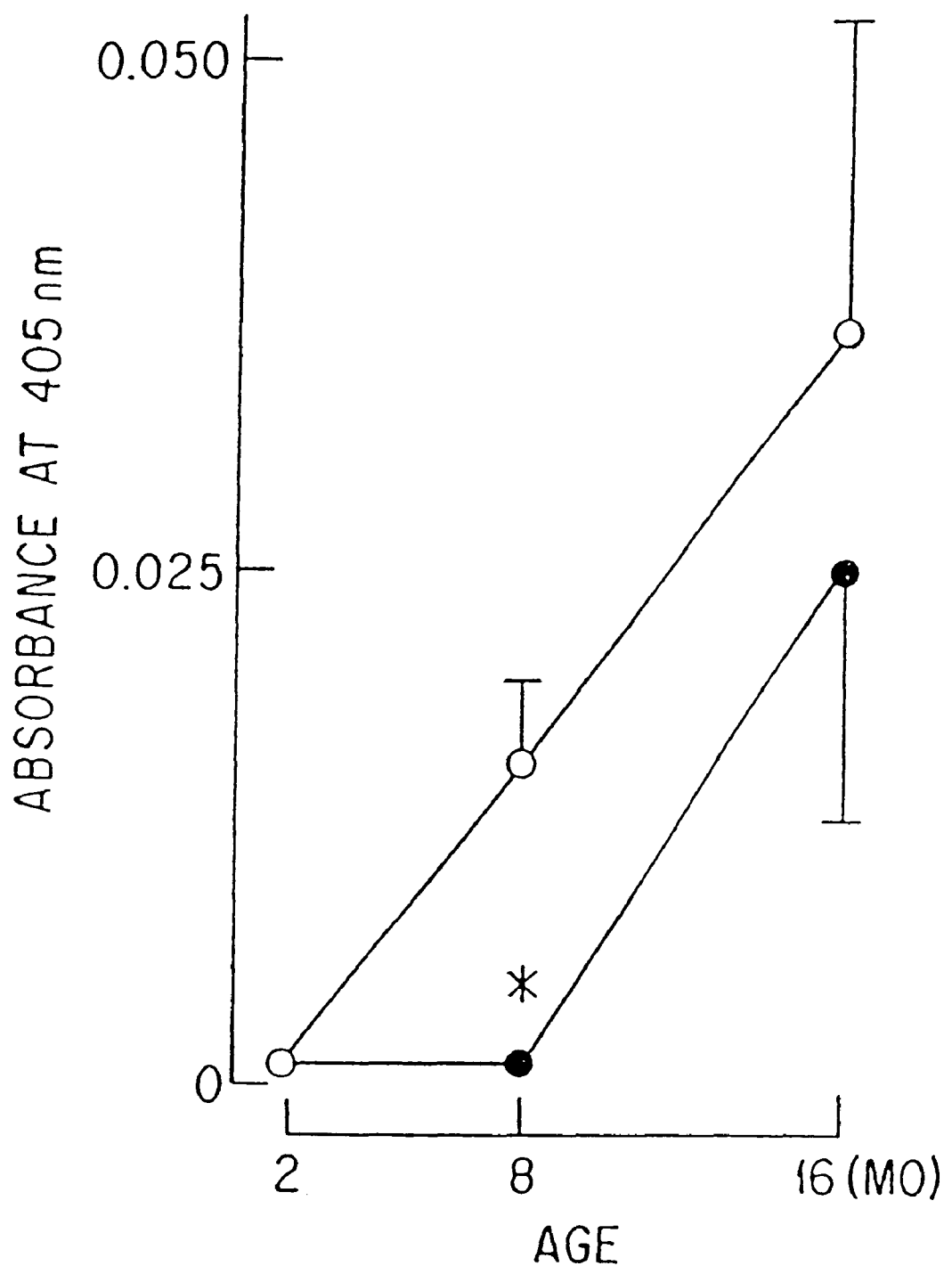
FIG. 4 illustrates serum level of antibodies to enteric bacteria. Five individual mice from each group; ○, control milk; ●, hyperimmune milk; were tested By ELISA. Level of antibodies indicates as absorbance measured with EIA reader at 405 nm. Each point and vertical bar represent $\bar{\chi}$ and SD. *Statistical difference was at p<0.005 from a group given control milk.

Hyperimmune milk suppressed the growth of intestinal Enterobacteriaceae (FIG. 3) and the appearance of anti-enteric bacterial antibodies in the serum (FIG. 4). It was found that hyperimmune milk protected mice irradiated with γ-ray from life-threatening intestinal bacterial infections. These results indicate that hyperimmune milk protects against translocation of intestinal bacteria from the intestinal tract. The hyperimmune milk was derived from cows which were hyperimmunized with mucosal bacteria (Table 2) and contained IgG specific for the intestinal bacteria antigens (Golay et al., Am. J. Clin. Nutr. 52:1014–1019 (1990)). These antibodies can cross-react with murine intestinal microflora. Therefore, the most effective component in hyperimmune milk may be antibodies specific for pathogenic enteric bacteria. Two hypotheses of the mechanism to inhibit the invasion of enteric bacteria are: (i) antibodies may sequentially activate complement components and directly lyse the bacteria or promote phagocytosis by polymorphonuclear leukocytes and/or macrophages in the intestinal lumen; and (ii) antibodies may aggregate bacteria and prevent the bacteria from adhering to the mucous membrane and from invading submucosal tissues (Janeway, A., Nature 333:804–806 (1988); Welsh et al., J. Pediatrics 94:1–9 (1978)). Hyperimmune milk also contained significantly higher levels of nonspecific anti-bacterial substances such as lactoperoxidase and lactoferin (Welsh et al., J. Pediatrics 94:1–9 (1978)). Therefore, these substances may also inhibit the invasion of enteric bacteria.

The present inventors have surprisingly discovered that the oral administration of hyperimmune milk significantly protected the immune function of GALT from age-related decline. Feeding hyperimmune milk protected the redirected cytolytic activity of IEL and the responsiveness of MLN cells to mitogenic and alloantigenic stimulation from age-related decline (FIGS. 7A–7B, 8 and 9). One explanation as to these findings is that alteration in intestinal bacterial population by hyperimmune milk may result in augmenting the immune function of GALT cells. Hyperimmune milk significantly inhibited the growth of Enterobacteriaceae, where Lactobacilli, an enteric bacterium known to be a potent nonspecific immune stimulant (Miake et al., Infect. Immun. 48:480–485 (1985); Nomoto et al., J. Clin. Lab. Immunol. 17:91–97 (1985)) was increased in mice fed hyperimmune milk (T. Ohmori et al., a manuscript in preparation). It would, thus, appear that hyperimmune milk may indirectly augment the immunological functions of GALT cells through increased stimulation of some enteric bacteria. Another explanation is that some components in hyperimmune milk such as cytokines may augment the immune function of the GALT cells (Welsh et al., J. Pediatrics 94:1–9 (1978)).

Figure 11:
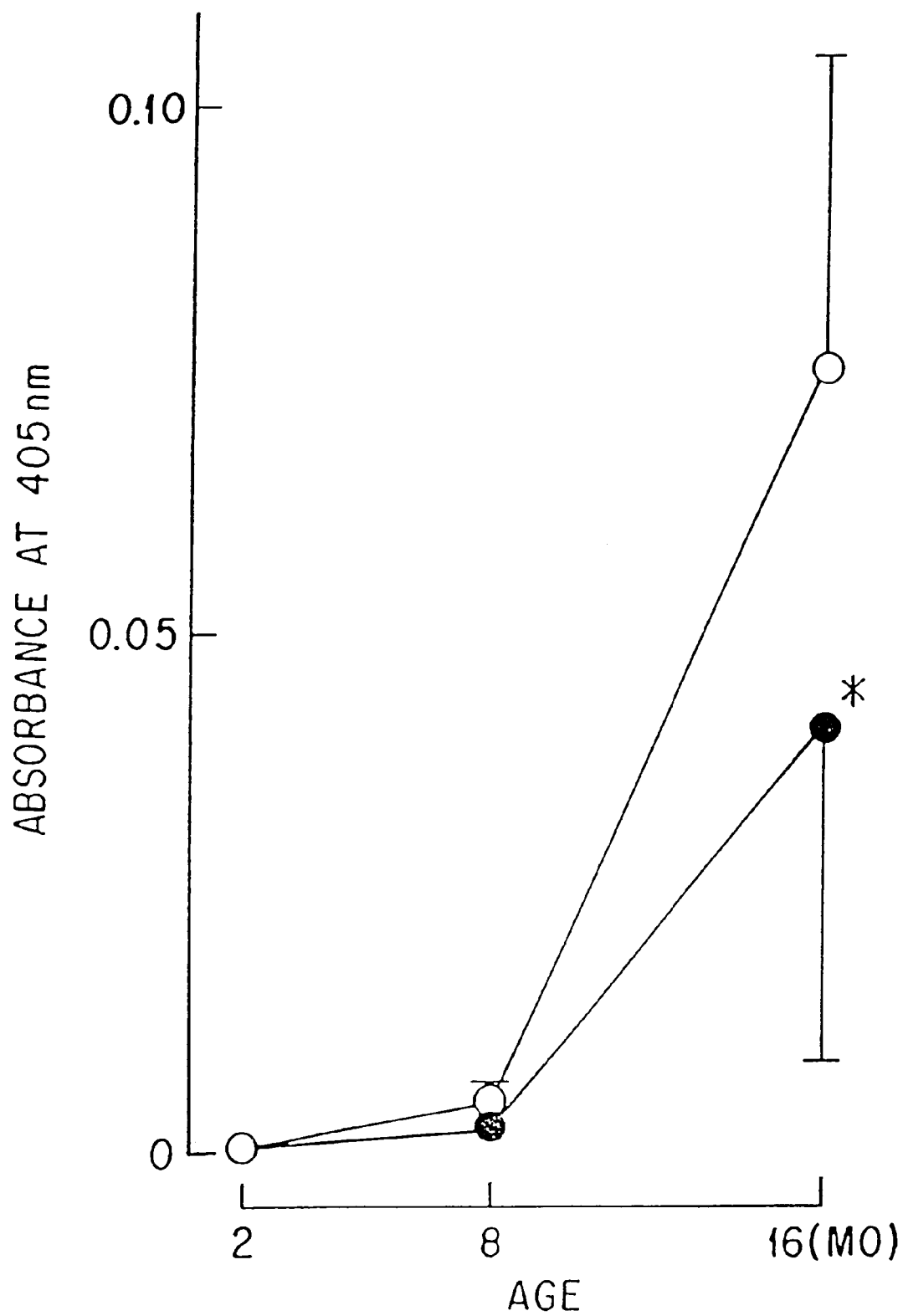
FIG. 11 illustrates serum level of autoantibodies to ssDNA. Five individual mice from each group; ○, control milk; ●, hyperimmune milk; were tested. Level of antibodies indicates as absorbance measured with EIA reader at 405 nm. Each point and vertical bar represent $\bar{\chi}$ and SD. Statistical difference was at p<0.1 from a group given control milk.

Hyperimmune milk also increased the number of anti-SRBC plaque forming cells in the spleen, in an early phase after immunization with SRBC (FIGS. 10A–10B). This result suggests that the protective action of hyperimmune milk in preventing the invasion of enteric bacteria for a long term, influences functions of systemic lymphoid tissues as well as those of GALT. The protective action of hyperimmune milk in preventing the appearance of serum autoantibodies to ssDNA (FIG. 11) supports the conclusion that hyperimmune milk influences systemic lymphoid tissue function indirectly.

In conclusion, oral administration of hyperimmune milk effectively protects an animal from the decline of immune function associated with aging. Clinically, these observations are important in the treatment of the elderly and the immunocompromised. Hyperimmune milk may be administered prophylactically to protect aged and immunocompromised patients from complexed forms of indigenous infections with enteric bacteria, for example, during treatment and/or amelioration of geriatric, or immunocomprising diseases such as leukemia.

Example 2

Preparation of S-100 Vaccine

A bacterial culture containing the spectrum of bacteria shown in Table 2 above, as obtained from the American Type Culture Collection was reconstituted with 15 ml of media and incubated overnight at 37° C. Once good growth was obtained, approximately one-half of the bacterial suspension was employed to inoculate one liter of broth with the inoculate being incubated at 37° C. The remaining suspension was transferred to sterile glycol tubes and stored at −20° C. for up to six months.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet obtained upon centrifugation was resuspended in a small amount of double distilled water.

The media-free bacterial suspension was heat-killed by placing the suspension in a glass flask in an 80° C. water bath overnight. The viability of the broth culture was tested with a small amount of heat-killed bacteria. Broth was inoculated with heat-killed bacteria, incubated at 37+ C. for five days and checked daily for growth, as the bacteria have to be killed for use in the vaccine.

The heat-killed bacteria were lyophilized until dry. The dry bacteria were then mixed with sterile saline solution to a concentration of $2.2 \times 10^8$ bacterial cells/ml saline (1.0 optical density reading at 660 nm).

Cows were given daily injections of 5 ml samples of the polyvalent liquid vaccine. Antibody (IgG) titer levels for the injected cattle were determined periodically by using an enzyme-linked immunoassay for bovine antibody against the polyvalent antigen.

Example 3

Immunization Procedures

Heat-killed bacteria were prepared in the manner described above. The polyvalent antigen sample (S-100) obtained was microencapsulated by a conventional phase-separation process to prepare a polyvalent antigen-containing microparticle product. Generally, the antigen-containing shaped matrix materials are formed from polymers of biocompatible material, preferably biodegradable or bioerodable materials, preferably polylactic acid, polyglycolic acid, copolymers of lactic and glycolic acids, polycaptolactone, copolyoxalates, proteins such as collagen, fatty acid esters of glycerol, and cellulose esters. These polymers are well known in the art and are described, for example, in U.S. Pat. Nos. 3,773,919; 3,887,699; 4,118,470; 4,076,798; all incorporated by reference herein. The polymeric matrix material employed was a biodegradable lactide-glycolide copolymer.

Heat-killed bacterial antigens are encapsulated in such matrix materials, preferably as microspheres of between 1–500 microns diameter, preferably 10–250 microns. The encapsulation processes are conventional and comprise phase separation methods, interfacial reactions, and physical methods. Many combinations of matrices and many concentrations of assorted antigens may be employed, in order to provide for optimal rates of release of bacterial antigens to the host body from the microparticles. These combinations can be determined by those skilled in the art without undue experimentation.

The microparticles in the example were less than 250 microns in diameter. Approximately 750 mg of microparticles containing 22% (16.5 mg) of polyvalent antigen was then suspended in about 3 cc of a vehicle (1 wt % Tween 20 and 2 wt % carboxymethyl cellulose in water).

A small group of cattle was selected from a larger herd of cattle. Five of these randomly selected cattle were selected as controls. Four cattle were injected intramuscularly with microparticles containing poly-valent antigen. Microparticle samples were sterilized with 2.0 mRad of gamma radiation. Antibody (IgG) titer levels were determined periodically from samples of cow's milk obtained from the inoculated cows, as well as from the control cows.

All of the publications cited herein are hereby incorporated by reference into the patent disclosure.

It will be appreciated by those skilled in the art that various modifications can be made without departing from the essential nature thereof. It is intended to encompass all such modifications within the scope of the appended claims.

What is new and claimed and intended to be covered by Letters Patent of the United States is:

1. A method for increasing the responsiveness of mesenteric lymph node (MLN) cells in an animal to mitogens as compared to said response in non-treated animals, comprising:
   orally administering to said animal hyperimmune milk, in an amount and for a time sufficient to increase the in vitro responsiveness to mitogens of said MLN cells to *Phaseolus vulgaris* agglutinin, wherein said hyperimmune milk is prepared from a cow immunized with an intestinal-bacteria-containing vaccine, said intestinal-bacteria containing vaccine comprising *Staph. aureus, Staph. epidermis, Strep. pyogenes,* A Type 1, *Strep. pyogenes,* A Type 3, *Strep. pyogenes,* A Type 5, *Strep. pyogenes,* A Type 8, *Strep. pyogenes,* A Type 12, *Strep. pyogenes,* A Type 14, *Strep. pyogenes,* A Type 18, *Strep. pyogenes,* A Type 22, *Aerobacter aerogenes, E. coli, Salmonella enteritidis, Pseudomonas aeruginosa, Klebsiella pneumoniae, Salmonella typhimurium, Haemophilus influenzae, Strep. mitis. Proteus vulgaris, Shigella dysenteriae, Strep. pneumoniae, Propionibacter acnes* (anaerobe) *Strep. sanguis, Strep. salvarius, Strep. mutans* and *Strep. agalactiae* bacteria.

2. A method for increasing the proliferative response of mesenteric lymph node (MLN) cells to alloantigens in an animal as compared to said response in non-treated animals, comprising:
   orally administering to said animal hyperimmune milk in an amount and for a time sufficient to increase the proliferative response of said MLN cells to allogeneic spleen cells in vitro, wherein said hyperimmune milk is prepared from a cow immunized with an intestinal-bacteria-containing vaccine, said intestinal-bacteria containing vaccine comprising *Staph. aureus, Staph. epidermis, Strep. pyogenes,* A Type 1, *Strep. pyogenes,* A Type 3, *Strep. pyogenes,* A Type 5, *Strep. pyogenes,* A Type 8, *Strep. pyogenes,* A Type 12, *Strep. pyogenes,* A Type 14, *Strep. pyogenes,* A Type 18, *Strep. pyogenes,* A Type 22, *Aerobacter aerogenes, E. coli, Salmonella enteritidis, Pseudomonas aeruginosa, Klebsiella pneumoniae, Salmonella typhimurium, Haemophilus influenzae, Strep. mitis. Proteus vulgaris, Shigella dysenteriae, Strep. pneumoniae, Propionibacter acnes* (anaerobe) *Strep. sanguis, Strep. salvarius, Strep. mutans* and *Strep. agalactiae* bacteria.

3. A method for increasing $CD4^+$ levels on gut-associated lymphoid tissue (GALT) cells in an animal as compared to said levels in non-treated animals, comprising:
   orally administering to said animal hyperimmune milk in an amount and for a time sufficient to increase said $CD^+$ levels, wherein said hyperimmune milk is prepared from a cow immunized with an intestinal-bacteria-containing vaccine, said intestinal-bacteria containing vaccine comprising *Staph. aureus, Staph. epidermis, Strep. pyogenes,* A Type 1, *Strep. pyogenes,* A Type 3, *Strep. pyogenes,* A Type 5, *Strep. pyogenes,* A Type 8, *Strep. pyogenes,* A Type 12, *Strep. pyogenes,* A Type 14, *Strep. pyogenes,* A Type 18, *Strep. pyogenes,* A Type 22, *Aerobacter aerogenes, E. coli, Salmonella enteritidis, Pseudomonas aeruginosa, Klebsiella pneumoniae, Salmonella typhimurium, Haemophilus influenzae, Strep. mitis. Proteus vulgaris, Shigella dysenteriae, Strep. pneumoniae, Propionibacter acnes* (anaerobe) *Strep. sanguis, Strep. salvarius, Strep. mutans* and *Strep. agalactiae* bacteria.

4. The method of any one of claims 1, 2 or 3 wherein said hyperimmune milk is administered orally.

5. The method of any one of claims 1, 2, or 3 wherein said animal is human.

6. The method of claim 4, wherein said hyperimmune milk is in the form of a skim milk powder and is administered in an amount of from about 1 to 200 g/kg body weight per day.

7. The method of claim 6, wherein said amount is from about 5 to 150 g/kg body weight per day.

8. The method of claim 7, wherein said amount is 98 g/kg body weight per day.

9. The method of claim 8, wherein said hyperimmune milk is administered for at least 6 months.

10. The method of claim 8, wherein said hyperimmune milk is administered for at least 14 months.

* * * * *